United States Patent [19]

Mackenzie et al.

[11] Patent Number: 5,741,790

[45] Date of Patent: Apr. 21, 1998

[54] AZETIDINES

[75] Inventors: Alexander Roderick Mackenzie; Allan Patrick Marchington; Donald Stuart Middleton; Sandra Dora Meadows, all of Sandwich, United Kingdom

[73] Assignee: Pfizer Inc., New York, N.Y.

[21] Appl. No.: 789,698

[22] Filed: Jan. 27, 1997

[30] Foreign Application Priority Data

Jan. 27, 1996 [GB] United Kingdom ............... 9601697

[51] Int. Cl.⁶ .................. A61K 31/495; A61K 31/535; C07D 401/14; C07D 413/14

[52] U.S. Cl. .................. 514/210; 544/121; 544/131; 544/364

[58] Field of Search .................. 544/131, 121, 544/364; 514/210

[56] References Cited

U.S. PATENT DOCUMENTS 5,607,930  3/1997  Loug et al. .................. 544/121

Primary Examiner—Robert W. Ramsuer
Attorney, Agent, or Firm—Peter C. Richardson; Paul H. Ginsburg; Garth Butterfield

[57] ABSTRACT

The present invention provides compounds of the formula (I):

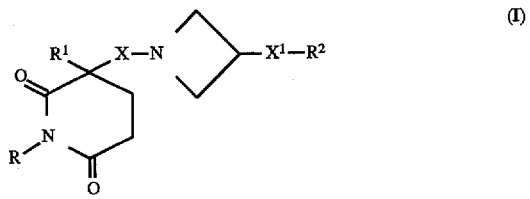

and the pharmaceutically acceptable salts thereof, wherein
R is $C_3$–$C_7$ cycloalkyl, aryl or $C_1$–$C_6$ alkyl, said $C_1$–$C_6$ alkyl being optionally substituted by fluoro, —COOH, —COO($C_1$–$C_4$) alkyl, $C_3$–$C_7$ cycloalkyl, adamantyl, aryl or het¹, and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro($C_1$–$C_4$) alkyl and fluoro ($C_1$–$C_4$)alkoxy;
$R^1$ is phenyl, benzyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;
$R^2$ represents various groups;
X is $C_1$–$C_4$ alkylene; and
$X^1$ is a direct link or $C_1$–$C_6$ alkylene.

Such compounds and salts are useful as tachykinin antagonists.

20 Claims, No Drawings

AZETIDINES

This invention relates to therapeutic agents of the glutarimide family. More particularly, this invention relates to azetidinylalkylglutarimide derivatives and to processes for the preparation of, intermediates used in the preparation of, compositions containing and uses of, such compounds.

International Patent Publication Number WO 96/05193 discloses various (azetidin-1-ylalkyl)lactams as tachykinin antagonists.

The present azetidinylalkylglutarimides are antagonists of tachykinins, including neurokinin A (NKA), neurokinin B (NKB) and Substance P, acting at the human neurokinin-1 ($NK_1$), neurokinin-2 ($NK_2$) or neurokinin-3 ($NK_3$) receptor, or a combination of two or more thereof. They are therefore useful for preventing or treating an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a disease caused by *Helicobacter pylori* or other urease positive Gram negative bacteria, a urogenital tract disorder such as incontinence, hyperreflexia, impotence or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a vasospastic disease such as angina or Reynaud's disease, a proliferative disorder such as cancer or a disorder involving fibroblast proliferation, a fibrosing or collagen disease such as scleroderma or eosinophillic fascioliasis, reflux sympathetic dystrophy such as shoulder/ hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Alzheimer's disease or multiple sclerosis, a disorder related to immune enhancement or suppression such as systemic lupus erythematosis, a rheumatic disease such as fibrositis, emesis, cough, acute or chronic pain, migraine, an opthalmic disease such as proliferative retinopathy, or a viral disease such as influenza or a cold.

The present derivatives are particularly potent and selective antagonists of tachykinins, including NKA, NKB and Substance P, acting at the human $NK_1$, $NK_2$ and $NK_3$ receptors or combinations of two or more thereof. They are particularly useful for treating or preventing an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a urogenital tract disorder such as incontinence or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain.

The present invention provides compounds of the formula (I):

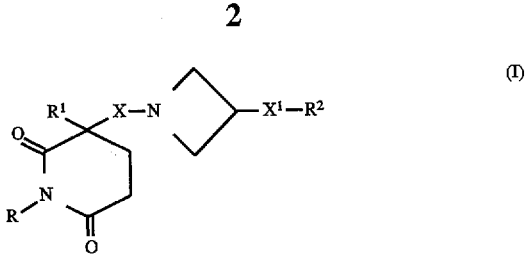

and the pharmaceutically acceptable salts thereof, wherein

R is $C_3$–$C_7$ cycloalkyl, aryl or $C_1$–$C_6$ alkyl, said $C_1$–$C_6$ alkyl being optionally substituted by fluoro, —COOH, —COO($C_1$–$C_4$) alkyl, $C_3$–$C_7$ cycloalkyl, adamantyl, aryl or het[1], and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro($C_1$–$C_4$) alkyl and fluoro ($C_1$–$C_4$)alkoxy;

$R^1$ is phenyl, benzyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;

$R^2$ is —$CO_2H$, —$CONR^3R^4$, —$CONR^5(C_3$–$C_7$ cycloalkyl), —$NR^5(C_2$–$C_5$ alkanoyl), —$NR^3R^4$, —$NR^5CONR^5R^6$, ($C_3$–$C_7$ cycloalkyl-$C_1C_4$ alkyl)$R^5N$—, ($C_3$–$C_7$ cycloalkyl-$C_1$–$C_4$ alkyl)$_2N$—, —$NR^5COCF_3$, —$NR^5(SO_2CF_3$, —$NR^5(SO_2C_1$–$C_4$ alkyl), —$NR^5SO_2NR^5R^6$, —$NR^5(SO_2$ aryl), —N(aryl) ($SO_2C_1$–$C_4$ alkyl), —$OR^5$, —$O(C_3$–$C_7$ cycloalkyl), —$SO_2 NR^5R^6$, het[3] or a group of the formula:

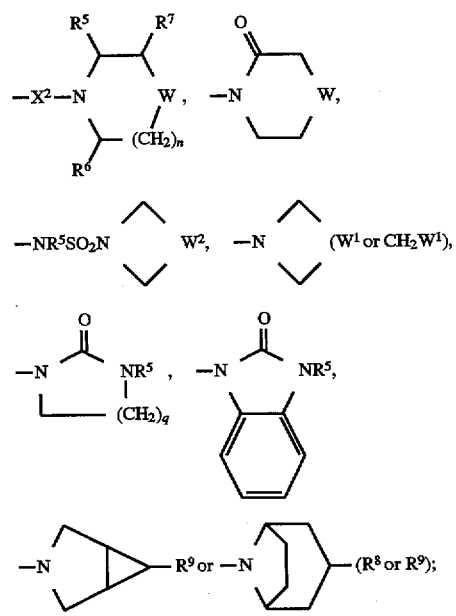

$R^3$ and $R^4$ are each independently selected from H and $C_1$–$C_4$ alkyl optionally substituted by hydroxy, $C_1$–$C_4$ alkoxy, —S(O)$_p$($C_1$–$C_4$ alkyl), amino, —NH($C_1$–$C_4$ alkyl), —N($C_1$–$C_4$ alkyl)$_2$ or het[2];

$R^5$ and $R^6$ are each independently selected from H, $C_1$–$C_4$ alkyl and $C_3$–$C_7$ cycloalkyl-$C_1$–$C_4$ alkyl, said $C_1$–$C_4$ alkyl and $C_3$–$C_7$ cycloalkyl-$C_1$–$C_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5$ ($SO_2C_1$–$C_4$ alkyl), —$NR^5SO_2NR^5R^6$, —$NR^5COO$ ($C_1$–$C_4$ alkyl), —$NR^5CONR^5R^6$, —$NR^5$ ($SO_2$morpholino), —$NR^5(SO_2$ aryl), —N(aryl) ($SO_2C_1$–$C_4$ alkyl) or a group of the formula:

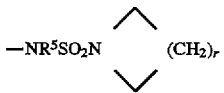

X is $C_1$–$C_4$ alkylene;

$X^1$ is a direct link or $C_1$–$C_6$ alkylene;

$X^2$ is a direct link, CO, $SO_2$ or $NR^5CO$ where the carbonyl is attached to the ring nitrogen atom;

W is methylene, CO, CH(OH), C(OH)$_2$, CH($C_1$–$C_4$ alkoxy), CHCO$_2$H, CHCO$_2$($C_1$–$C_4$ alkyl), CHCONR$^5$R$^6$, CHF, CF$_2$, CH(azetidin-1-yl), CH(pyrrolidin-1-yl), CH(piperidin-1-yl), CH(morpholino), CH(benzoxazol-2-yl), CHR$^9$, O, S(O)$_p$, NR$^5$, N(C$_3$–C$_7$ cycloalkyl), NSO$_2$(C$_1$–C$_4$ alkyl), NSO$_2$NR$^5$R$^6$, NSO$_2$CF$_3$, NSO$_2$(morpholino), NSO$_2$(aryl),

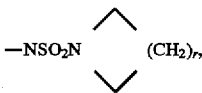

NCONR$^5$R$^6$, NCOR$^5$, NCO(aryl) or NCO$_2$(C$_1$–C$_4$ alkyl);

$W^1$ is methylene, CO, CH(OH), C(OH)$_2$, CH($C_1$–$C_4$ alkoxy), CHCO$_2$H, CHCO$_2$($C_1$–$C_4$ alkyl), CHCONR$^5$R$^6$, CHF, CH(azetidin-1-yl), CH(pyrrolidin-1-yl), CH(piperidin-1-yl), CH(morpholino) or CHR$^9$;

$W^2$ is $W^1$, —CH$_2$W$^1$—, —CH$_2$WCH$_2$— or —CH$_2$CH$_2$WCH$_2$—;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R^9$ and W, means naphthyl or phenyl, each optionally substituted by $C_1$–$C_4$ alkyl, halo, —OR$^5$, fluoro($C_1$–$C_4$)alkyl, $C_2$–$C_5$ alkanoyl, —CONR$^5$R$^6$, —SO$_2$ NR$^5$R$^6$ or phenyl;

"het$^1$", used in the definition of R, means thienyl or a 5- or 6-membered ring heteroaryl group containing either 1 or 2 nitrogen heteroatoms or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro ($C_1$–$C_4$ alkyl) and fluoro($C_1$–$C_4$ alkoxy); "het$^2$", used in the definitions of $R^3$ and $R^4$, means a 4- to 7-membered ring, non-aromatic, heterocyclic group containing 1 or 2 heteroatoms each independently selected from nitrogen, oxygen and S(O)$_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —CONR$^5$R$^6$ or —SO$_2$NR$^5$R$^6$ substituent;

and "het$^3$", used in the definition of $R^2$ means an optionally benzo-fused, N-linked, 5-membered ring heteroaryl group containing from 1 to 4 nitrogen heteroatoms, which het$^3$ is optionally substituted, including in the benzo-fused portion, by 1 or 2 substituents each independently selected from $C_1$–$C_4$ alkyl, fluoro and fluoro($C_1$–$C_4$)alkyl.

In the above definitions, the term "halo" means fluoro, chloro, bromo or iodo and alkyl, alkylene and alkoxy groups containing three or more carbon atoms and alkanoyl groups containing four or more carbon atoms can be straight- or branched-chain.

Preferably R is aryl, optionally substituted $C_3$–$C_7$ cycloalkyl, or is $C_1$–$C_6$ alkyl substituted by aryl or optionally substituted $C_3$–$C_7$ cycloalkyl.

More preferably, R is optionally substituted $C_3$–$C_7$ cycloalkyl or $C_1$–$C_6$ alkyl substituted by optionally substituted $C_3$–$C_7$ cycloalkyl.

Most preferably R is 2-cyclopropylethyl, cyclohexyl, 4,4-difluorocyclohexyl, cyclohexylmethyl or cyclopropylmethyl.

Preferably, $R^1$ is phenyl optionally substituted by 1 or 2 halo substituents.

More preferably, $R^1$ is phenyl optionally substituted by 1 or 2 substituents each independently selected from fluoro and chloro.

Yet more preferably, $R^1$ is phenyl, 3,4-difluorophenyl, 3-chlorophenyl, 4-chlorophenyl or 3,4-dichlorophenyl.

Most preferably, $R^1$ is 3,4-dichlorophenyl.

Preferably, $R^2$ is —CONR$^3$R$^4$, —CONR$^5$(C$_3$–C$_7$ cycloalkyl), —NR$^3$R$^4$, het$^3$ or a group of the formula:

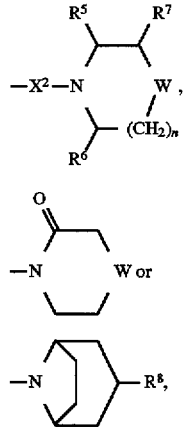

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CHF, CO, CH($C_1$–$C_4$ alkoxy), CHCO$_2$H, CHCO$_2$ ($C_1$–$C_4$ alkyl), CH(benzoxazol-2-yl), CHNR$^5$R$^6$, CHNR$^5$COR$^5$, CHNR$^5$(SO$_2$C$_1$–C$_4$ alkyl), CHNR$^5$COO ($C_1$–$C_4$ alkyl), O, S(O)$_p$, NR$^5$, NSO$_2$(C$_1$–C$_4$ alkyl), NSO$_2$NR$^5$R$^6$, NSO$_2$(morpholino), NSO$_2$(piperidino), NCONR$^5$R$^6$, NCOR$^5$, NCO(aryl) or NCO$_2$(C$_1$–C$_4$ alkyl), n is 1 or 2 when W is other than methylene and is 0 or 1 when W is methylene, and p is 0, 1 or 2.

More preferably, $R^2$ is —CONR$^3$R$^4$, —CONR$^5$(C$_3$–C$_7$ cycloalkyl), —NR$^3$R$^4$, a N-linked, 5-membered ring heteroaryl group containing 1 or 2 nitrogen heteroatoms, or a group of the formula:

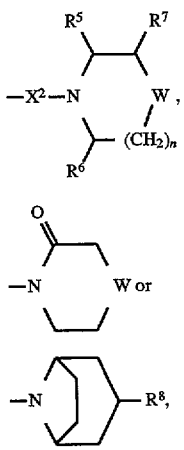

where $R^3$ and $R^4$ are each independently selected from methyl and $C_1$-$C_4$ alkyl substituted by hydroxy or methoxy, $R^5$ and $R^6$ are each independently selected from H, methyl, trifluoromethyl and cyclopropylmethyl, $R^7$ is H, hydroxy or phenyl, $R^8$ is hydroxy or acetyloxy, W is methylene, CH(OH), CHOCH$_3$, CHF, CO, CHOCH$_2$CH$_3$, CHO(CH$_2$)$_2$CH$_3$, CHOC(CH$_3$)$_3$, CHCO$_2$H, CHCO$_2$CH$_3$, CHCO$_2$CH$_2$CH$_3$, CH(benzoxazol-2-yl), CHNH$_2$, CHNHCH$_2$(cyclopropyl), CHNHCOCH$_3$, CHNHSO$_2$CH$_3$, CHNHCO$_2$C(CH$_3$)$_3$, O, S(O)$_p$, NH, NCH$_3$, NCH$_2$ (cyclopropyl), NSO$_2$CH$_3$, NSO$_2$NH$_2$, NSO$_2$NHCH$_3$, NSO$_2$N(CH$_3$)$_2$, NSO$_2$(morpholino), NSO$_2$(piperidino), NCONH$_2$, NCONHCH$_3$, NCOCH$_3$, NCOCF$_3$, NCO (phenyl) or NCO$_2$C(CH$_3$)$_3$, n is 1 or 2 when W is other than methylene and is 0 or 1 when W is methylene, and p is 0, 1 or 2.

Yet more preferably, $R^2$ is N-(2-methoxyethyl)-N-methylcarbamoyl, N-cyclohexylcarbamoyl, N-(2-hydroxyethyl)-N-methylamino, N-(2-hydroxy-2-methylpropyl)-N-methylamino, N-(2-methoxyethyl)-N-methylamino, imidazol-1-yl, 3-hydroxypyrrolidin-1-yl, piperidin-1-yl, 2,6-dimethylpiperidin-1-yl, 3-hydroxypiperidin-1-yl, 4-hydroxypiperidin-1-yl, 4-methoxypiperidin-1-yl, 4-ethocypiperidin-1-yl, 4-(n-propoxy)piperidin-1-yl, 4-(t-butoxy)piperidin-1-yl, 4-carboxypiperidin-1-yl, 4-methoxycarbonylpiperidin-1-yl, 4-ethoxycarbonylpiperidin-1-yl, 4-(benzoxazol-2-yl)piperidin-1-yl, 4-aminopiperidin-1-yl, 4-cyclopropylmethylaminopiperidin-1-yl, 4-acetamidopiperidin-1-yl, 4-methanesulphonamidopiperidin-1-yl, 4-(t-butoxycarbonylamino)piperidin-1-yl, morpholino, 2-phenylmorpholino, homomorpholino, thiomorpholino, 1-oxothiomorpholino, 1,1-dioxothiomorpholino, piperazin-1-yl, 4-methylpiperazin-1-yl, 4-cyclopropylmethylpiperazin-1-yl, 4-methanesulphonylpiperazin-1-yl, 4-aminosulphonylpiperazin-1-yl, 4-methylaminosulphonylpiperazin-1-yl, 4-dimethylaminosulphonylpiperazin-1-yl, 4-morpholinosulphonylpiperazin-1-yl, 4-piperidinosulphonylpiperazin-1-yl, 4-carbamoylpiperazin-1-yl, 4-N-methylcarbamoylpiperazin-1-yl, 4-acetylpiperazin-1-yl, 4-trifluoroacetylpiperazin-1-yl, 4-benzoylpiperazin-1-yl, 4-(t-butoxycarbonyl)piperazin-1-yl, pyrrolidin-1-ylcarbonyl, piperidin-1-ylcarbonyl, 3-oxomorpholino, 3-hydroxy-8-azabicyclo[3.2.1]oct-8-yl, 3-acetyloxy-8-azabicyclo[3.2.1]oct-8-yl, 4-fluoropiperidin-1-yl or 4-oxopiperidin-1-yl.

Most preferably, $R^2$ is 4-aminopiperidin-1-yl, 4-carboxypiperidin-1-yl, 4-hydroxypiperidin-1-yl, morpholino, 1-oxothiomorpholino, 4-aminosulphonylpiperazin-1-yl, 4-methanesulphonylpiperazin-1-yl, 4-dimethylaminosulphonylpiperazin-1-yl, 4-morpholinosulphonylpiperazin-1-yl, 4-piperidinosulphonylpiperazin-1-yl, 4-fluoropiperidin-1-yl or 4-oxopiperidin-1-yl.

Preferably, X is ethylene or propylene.
Preferably, $X^1$ is a direct link.
Preferably, $X^2$ is a direct link.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1–19 (1977).

A compound of the formula (I) may contain one or more asymmetric carbon atoms and may therefore exist in two or more stereoisomeric forms. The present invention includes the individual stereoisomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

The preferred compounds of the formula (I) and salts thereof have the stereochemistry shown below in formula (IA) at the position of attachment of the X and $R^1$ groups to the glutarimide ring:

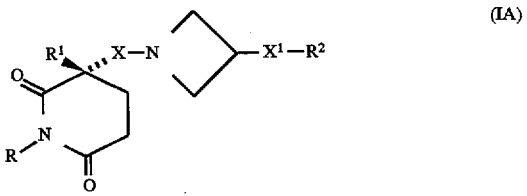

Preferred examples of a compound of formula (I) are those wherein:

(i) R is cyclohexylmethyl, $R^1$ is 3,4-dichlorophenyl, X is ethylene, $X^1$ is a direct link and $R^2$ is morpholino;

(ii) R is cyclohexylmethyl, $R^1$ is 3,4-dichlorophenyl, X is ethylene, $X^1$ is a direct link and $R^2$ is 4-aminosulphonylpiperazin-1-yl;

(iii) R is cyclopropylmethyl, $R^1$ is 3,4-dichlorophenyl, X is ethylene, $X^1$ is a direct link and $R^2$ is 4-morpholinosulphonylpiperazin-1-yl;

(iv) R is cyclopropylmethyl, $R^1$ is 3,4-dichlorophenyl, X is ethylene, $X^1$ is a direct link and $R^2$ is 4-aminosulphonylpiperazin-1-yl;

(v) R is cyclopropylmethyl, $R^1$ is 3,4-dichlorophenyl, X is ethylene, $X^1$ is a direct link and $R^2$ is 4-dimethylaminosulphonylpiperazin-1-yl;

(vi) R is cyclopropylmethyl, $R^1$ is 3,4-dichlorophenyl, X is ethylene, $X^1$ is a direct link and $R^2$ is 4-piperidinosulphonylpiperazin-1-yl;

(vii) R is cyclopropylethyl, $R^1$ is 3,4-dichlorophenyl, X is ethylene, $X^1$ is a direct link and $R^2$ is 4-aminosulphonylpiperazin-1-yl; or (viii) R is cyclopropylethyl, $R^1$ is 3,4-dichlorophenyl, X is ethylene, $X^1$ is a direct link and $R^2$ is morpholino;

or any such compound with the stereochemistry shown above for the compound of the formula (IA) at the position of attachment of the X and $R^1$ groups to the glutarimide ring, or a pharmaceutically acceptable salt of any thereof.

The compounds of the formula (I) provided by the invention can be prepared by the following methods:

1) The compounds of the formula (I) where X is $(C_0–C_3$ alkylene)$CH_2$—, the methylene group of which is attached to the azetidine nitrogen atom, and R, $R^1$, $R^2$ and $X^1$ are as previously defined for a compound of the formula (I) can be prepared by reductive amination using as starting materials a compound of the formula:

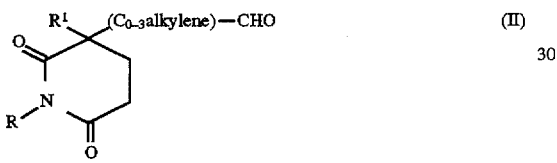

where R and $R^1$ are as previously defined for a compound of the formula (I), and a compound of the formula:

or an acid addition salt thereof, where $R^2$ and $X^1$ are as previously defined for a compound of the formula (I). The reaction is preferably carried out in the presence of a suitable acid, e.g. acetic acid.

The reaction proceeds via the initial formation of an intermediate iminium species of the formula:

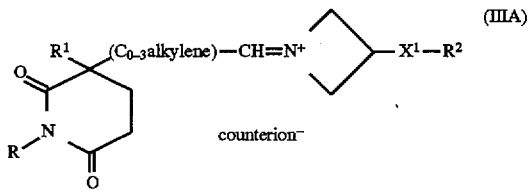

where the counterion depends on the acid species present in the reaction, and can for example be OH or $CH_3CO_2$. The species of formula (IIIA) may be stable and isolatable. The reaction is preferably carried out without isolation of the intermediate of the formula (IIIA) in which case it is reduced in situ to provide a compound of formula (I).

In a typical procedure, an aldehyde of the formula (II) is first reacted with an azetidine of the formula (III) in a suitable solvent, e.g. tetrahydrofuran, and the mixture then treated with a suitable reducing agent, e.g. sodium triacetoxyborohydride or sodium cyanoborohydride, in the presence of a suitable acid, e.g. acetic acid, to give the required product. If an acid addition salt of an azetidine of the formula (III) is used as a starting material, a suitable acid acceptor, e.g. triethylamine, can be added prior to the addition of the reducing agent.

The reaction is typically carried out at room temperature.

The starting aldehydes of the formula (II) can be prepared by the method shown in the Scheme below:

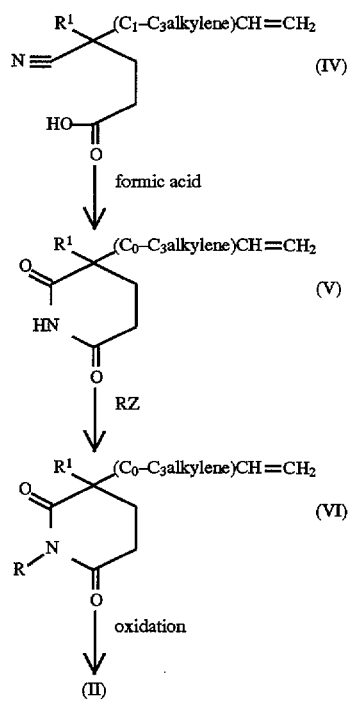

where R and $R^1$ are as previously defined for a compound of the formula (I) and Z is a suitable leaving group, e.g. chloro, bromo, iodo, methanesulphonyloxy, p-toluenesulphonyloxy or trifluoromethylsulphonyloxy.

Starting materials of formula (IV) where $R^1$ is as defined for compounds of formula (I) can be made by conventional methods such as by adaptation of the methods described in the Experimental section.

Glutarimides of formula (V) where $R^1$ is as defined for compounds of formula (I) can be made by reaction of compounds of formula (IV) with formic acid. The reaction is preferably carried out in the presence of an aqueous acid such as hydrochloric acid, and a polar solvent such as N,N-dimethylformamide, preferably at elevated temperatures. N-Substituted glutarimides of formula (VI) can be made from compounds of formula (V) by reaction with reagents RZ, where R is as defined for compounds of formula (I), and Z is as defined above. Preferably, Z is bromo. The reaction is preferably carried out in the presence of a base, such as sodium hydride, in a polar solvent such as N,N-dimethylformamide, at elevated temperatures. The alkene moiety of the compounds of formula (VI), where R and $R^1$ are as previously defined, can then be oxidised, for example by ozonolysis using a dimethyl sulphide work-up, to give aldehydes (II).

The reagents of the formula RZ can be prepared by conventional methods such as by adaptation of the preparations described hereafter and in "Advanced Organic Chemistry" by J. March (3rd edn., Wiley-Interscience) and the references therein.

The starting azetidines of the formula (III) may be prepared by conventional methods.

2) All the compounds of the formula (I), where X, X$^1$, R, R$^1$ and R$^2$ are as previously defined for a compound of the formula (I), can be prepared by reaction of a compound of the formula (VII):

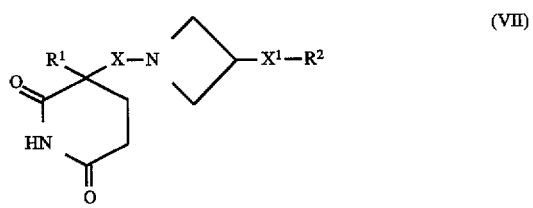 (VII)

where X, X$^1$, R$^1$ and R$^2$ are as previously defined for a compound of the formula (I), with a compound of the formula RZ, where R and Z are as previously defined and the reactions are carried out in a similar manner to those described earlier for the transformation (V) to (VI).

The reagents of the formula RZ can be prepared by conventional methods such as by adaptation of the preparations described hereafter and in "Advanced Organic Chemistry" by J. March (3rd edn., Wiley-Interscience) and the references therein.

3) All the compounds of the formula (I) where X, X$^1$, R, R$^1$ and R$^2$ are as previously defined for a compound of the formula (I) can be prepared by reaction of a compound of the formula (VIII):

 (VIII)

where X, R and R$^1$ are as previously defined for a compound of the formula (I) and Z$^3$ is a suitable leaving group, e.g. chloro, bromo, iodo, methanesulphonyloxy, trifluoromethanesulphonyloxy or p-toluenesulphonyloxy, with a compound of the formula:

 (III)

where R$^2$ and X$^1$ is as previously defined for a compound of the formula (I).

In a typical procedure, a compound of the formula (VIII) where Z$^3$ is preferably methanesulphonyloxy, is reacted with a compound of the formula (III) in the presence of a suitable acid acceptor, e.g. triethylamine or potassium carbonate or a combination thereof, in a suitable solvent, e.g. acetonitrile, and at about the reflux temperature thereof.

The compound of the formula (III) can be prepared in situ from an acid addition salt thereof by using a molar excess of the acid acceptor.

The starting materials of the formula (VIII) may be prepared by conventional methods such as by hydroxy group functional transformation of alcohols of formula (VIIIa):

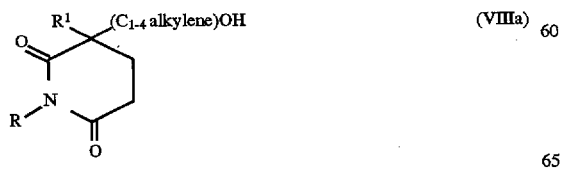 (VIIIa)

where R and R$^1$ are as described earlier for compounds of formula (I), for example where Z$^3$ is methanesulphonyloxy by reaction of an alcohol of formula (VIIIa) with methanesulphonyl chloride in the presence of a suitable acid acceptor such as triethylamine. The alcohol of formula (VIIIa) may be prepared by reduction of an aldehyde of formula (II) as defined above in Method 1, using conventional methods, such as those described in J. March, Advanced Organic Chemistry, 3rd edition, Wiley Interscience, for example by reaction with a suitable reducing agent such as zinc borohydride in a suitable solvent such as tetrahydrofuran.

4) The compounds of the formula (I) where R$^1$ is phenyl and X, X$^1$, R and R$^2$ are as previously defined for a compound of the formula (I) can be prepared by hydrogenolysis of a compound of the formula (I) where R$^1$ is phenyl substituted by chloro, bromo or iodo and X, X$^1$, R and R$^2$ are as previously defined for a compound of the formula (I).

In a typical procedure the hydrogenolysis is carried out in ammoniacal ethanol using a suitable catalyst, e.g. Raney nickel or, preferably, palladium-on-carbon, at about 50° C. and under an atmosphere of hydrogen at about 345 kPa (50 psi).

5) The compounds of the formula (I) where R$^2$ is a group of the formula:

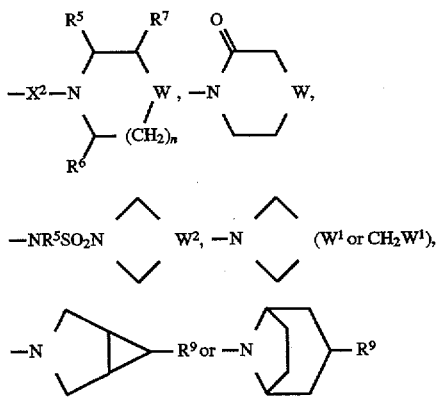

R$^9$ is —NHR$^5$, W is NH or CHNHR$^5$, W$^1$ is CHNHR$^5$, W$^2$ is W$^1$, —CH$_2$W$^1$—, —CH$_2$WCH$_2$— or —CH$_2$CH$_2$WCH$_2$—, and X, X$^1$, X$^2$, R, R$^1$, R$^5$, R$^6$, R$^7$ and n are as previously defined for a compound of the formula (I), can be prepared by deprotection of a compound of the formula (IX):

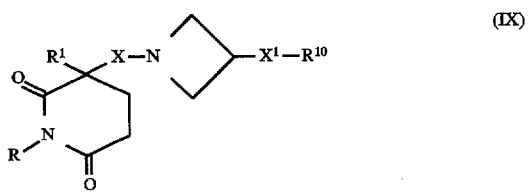 (IX)

where R$^{10}$ is a group of the formula:

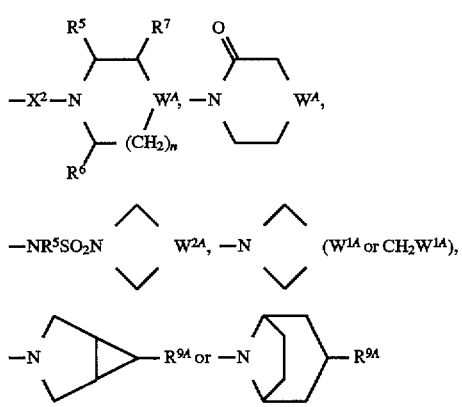

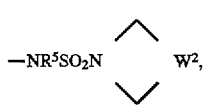

respectively, $R^{9A}$ is —$NZ^4R^5$, $W^A$ is $NZ^4$ or $CHNZ^4R^5$, $W^{1A}$ is $CHNZ^4R^5$, $W^{2A}$ is $W^{1A}$, —$CH_2W^{1A}$—, —$CH_2W^ACH_2$— or —$CH_2CH_2W^ACH_2$—, X, $X^1$, $X^2$, R, A, $R^1$, $R^4$, $R^5$, $R^6$, $R^7$, m and n are as previously defined for a compound of the formula (I) and $Z^4$ is a suitable protecting group, e.g. t-butoxycarbonyl (e.g. a compound of the formula (I) where W is $NCO_2C(CH_3)_3$ or $R^9$ is —$NR^5CO_2C(CH_3)_3$) or benzyloxycarbonyl.

Suitable protecting groups that may be used in this Method, together with methods for deprotection, are well known to the skilled person, e.g. see Greene et al, "Protective Groups in Organic Synthesis", Second Edition, 1991, Wiley-Interscience.

In a typical procedure where $Z^4$ is t-butoxycarbonyl, the deprotection can be carried out using trifluoroacetic acid in a suitable solvent, e.g. dichloromethane, at room temperature.

The starting materials of the formula (IX) can be prepared by conventional methods such as by appropriate adaptation of the Methods described herein for preparing the compounds of the formula (I).

6) The compounds of the formula (I) where $R^2$ is a group of the formula:

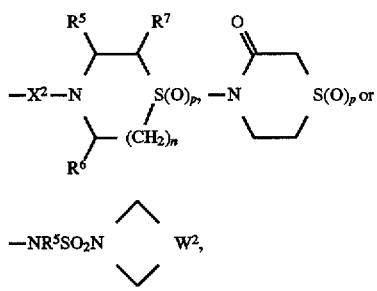

where p is 1 or 2, $W^2$ is —$CH_2S(O)_pCH_2$— or —$CH_2CH_2S(O)_pCH_2$— and X, $X^1$, $X^2$, R, $R^1$, $R^5$, $R^6$, $R^7$ and n are as previously defined for a compound of the formula (I) can be prepared by oxidation of a compound of the formula (I) where $R^2$ is a group of the formula:

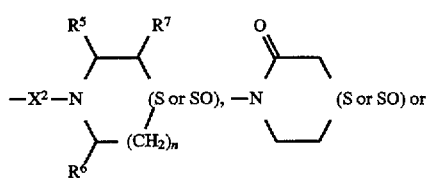

as appropriate, wherein $W^2$ is —$CH_2$(S or SO)$CH_2$— or —$CH_2CH_2$(S or SO)$CH_2$—, and X, $X^1$, $X^2$, R, $R^1$, $R^5$, $R^6$, $R^7$ and n are as previously defined for a compound of the formula (I). The oxidation is carried out with at least one molar equivalent of a suitable oxidising agent when converting a sulphoxide to a sulphone, at least two molar equivalents of a suitable oxidising agent when converting a sulphide to a sulphone and substantiality one molar equivalent of a suitable oxidising agent for the conversion of a sulphide to a sulphoxide.

Suitable oxidising agents and conditions for this purpose are aqueous hydrogen peroxide solution under basic conditions (e.g. in the presence of potassium carbonate, acetonitrile and using methanol as the solvent) or m-chloroperbenzoic acid in a suitable solvent, e.g. dichloromethane.

7) The compounds of the formula (I) where $R^2$ is a group of the formula:

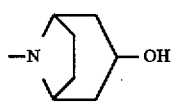

and X, $X^1$, R and $R^1$ are as previously defined for a compound of the formula (I), can be prepared by deprotection of a compound of the formula (X):

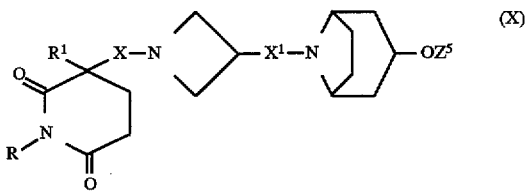

where $Z^5$ is a suitable protecting group, e.g. acetyl (i.e. a compound of the formula (I) where $R^8$ is acetyloxy) or tetrahydropyran-2-yl, and X, $X^1$, R and $R^1$ are as previously defined for a compound of the formula (I).

Suitable protecting groups that may be used for this Method, together with methods for deprotection, are well known to the skilled person, e.g. see Greene et al, "Protective Groups in Organic Synthesis", Second Edition, 1991, Wiley-Interscience.

In a typical procedure where $Z^5$ is acetyl the deprotection can be carried out using an aqueous alcoholic solution of a suitable strong base, e.g. sodium hydroxide. The reaction is typically carried out in aqueous methanol at about room temperature.

The starting materials of the formula (X) can be prepared by conventional methods such as by adaptation of the Methods described herein for preparing the compounds of the formula (I).

8) The compounds of the formula (I) where $X^1$ is a direct link and $R^2$ is —$NR^3R^4$, ($C_3$-$C_7$ cycloalkyl-$C_1$-$C_4$ alkyl) $R^5N$—, or is a group of the formula:

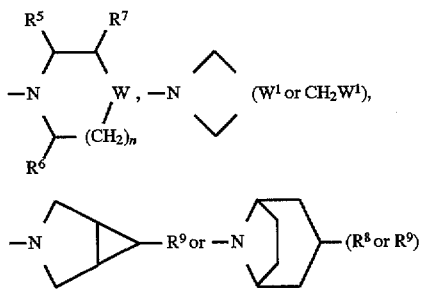

and X, W, W¹, R, R¹, R³, R⁴, R⁵, R⁶, R⁷, R⁸, R⁹ and n are as previously defined for a compound of the formula (I), can be prepared by reaction of a compound of the formula (XI):

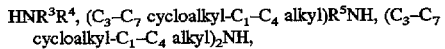
(XI)

where X, R and R¹ are as previously defined for a compound of the formula (I) and $Z^7$ is a suitable leaving group, e.g. methanesulphonyloxy or p-toluenesulphonyloxy, with a compound of the formula:

HNR³R⁴, (C₃–C₇ cycloalkyl-C₁–C₄ alkyl)R⁵NH, (C₃–C₇ cycloalkyl-C₁–C₄ alkyl)₂NH,

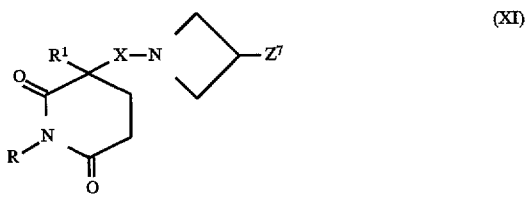

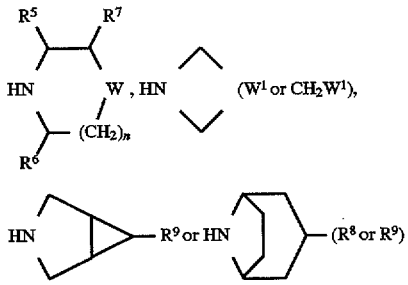

respectively, where W, W¹, R³, R⁴, R⁵, R⁶, R⁷, R⁸, R⁹ and n are as previously defined for a compound of the formula (I).

In a typical procedure, the reaction is carried out using an excess of the amine and in a suitable solvent, e.g. acetonitrile or dichloromethane, and at the reflux temperature of the solvent. Alternatively, a further suitable acid acceptor, e.g. potassium carbonate, can be added to the reaction mixture.

The starting amines can be prepared by conventional methods.

The starting materials of the formula (XI) can also be prepared by conventional methods such as by reductive amination using as starting materials a compound of the formula (II) and ammonia to prepare the corresponding primary amine, reaction of the amine with epichlorohydrin or 1,3-dichloropropan-2-ol to prepare the corresponding azetidin-3-ol derivative, followed by hydroxy functional group interconversion to provide a compound of the formula (XI).

9) The compounds of the formula (I) where X, X¹, R, R¹ and R² are as previously defined for Method (8) can be prepared by reductive amination using as starting materials a compound of the formula (XII):

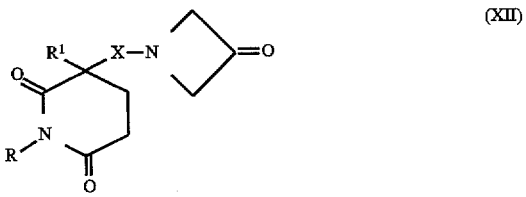
(XII)

where X, R and R¹ are as previously defined for a compound of the formula (I), and a compound of the formula:

HNR³R⁴, (C₃–C₇ cycloalkyl-C₁–C₄ alkyl)R⁵NH,

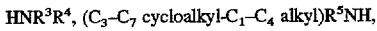

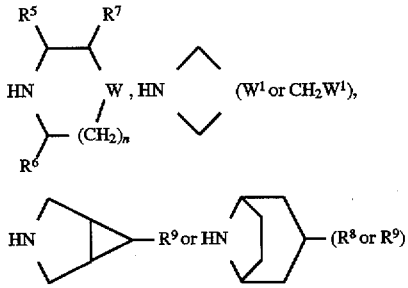

as appropriate, or an acid addition salt thereof, where W, W¹, R³, R⁴, R⁵, R⁶, R⁷, R⁸, R⁹ and n are as previously defined for a compound of the formula (I). The reaction is preferably carried out in the presence of a suitable acid, e.g. acetic acid.

A typical procedure that can be followed is described in Method (1).

If a primary amine is used, the reaction proceeds via an imine intermediate. If a secondary amine is used, the reaction proceeds via an intermediate iminium species (cf. a compound of the formula (IIIA)). Both the imine and iminium species may be stable and isolatable. The reaction is preferably carried out without isolation of the imine or iminium salt intermediate in which case it is reduced in situ to provide a compound of the formula (I).

The starting materials of the formula (XII) can be prepared by oxidation of a compound of the formula (XI; $Z^7$ is OH) using a suitable oxidation regime, such as a Swern oxidation.

10) Certain compounds of the formula (I) can be prepared by derivatisation of certain amines of the formula (I). For example, a compound of the formula (I) wherein R² is

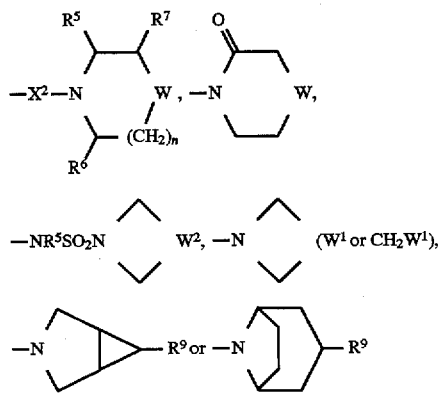

wherein W is NH or CHNHR⁵, W¹ is CHNHR⁵, W² is W¹, —CH₂W¹—, —CH₂WCH₂— or —CH₂CH₂WCH₂—, or R⁹ is —NHR⁵ and X, X¹, X², R, R¹, R⁵, R⁶, R⁷ and n are as previously defined for a compound of the formula (I), may be converted to (a) a compound of the formula (I) wherein W is $NR^5$ or $CHNR^5R^6$, $W^1$ is $CHNR^5R^6$ or $R^9$ is $-NHR^5$, or an acid addition salt thereof, as appropriate, wherein $R^5$ and $R^6$ are as previously defined for a compound of the formula (I) with the provisos that $R^5$ is not H and it has a methylene group bonded to the nitrogen atom, by reductive amination with an aldehyde of the formula $(C_1-C_3\text{ alkyl})CHO$ or $(C_3-C_7\text{ cycloalkyl-}C_1-C_3\text{ alkyl})CHO$, said $C_1-C_3$ alkyl and $(C_3-C_7\text{ cycloalkyl-}C_1-C_3\text{ alkyl})$ being optionally substituted by fluoro.

Suitable conditions for this conversion are described in Method (1);

(b) a compound of the formula (I) wherein W is $NCONHR^6$ or $CHNR^5CONHR^6$, $W^1$ is $CHNR^5CONHR^6$ or $R^9$ is $-NR^5CONHR^6$, as appropriate, wherein $R^5$ and $R^6$ are as previously defined for a compound of the formula (I) with the proviso that $R^6$ is not H, by reaction with an isocyanate of the formula:

$R^6NCO$ wherein $R^6$ is as previously defined for this Method.

The reaction is typically carried out using a suitable solvent, e.g. dichloromethane or tetrahydrofuran;

(c) a compound of the formula (I) wherein W is $NSO_2CF_3$ or $CHNR^5SO_2CF_3$, $W^1$ is $CHNR^5SO_2CF_3$ or $R^9$ is $-NR^5SO_2CF_3$, as appropriate, wherein $R^5$ is as previously defined for a compound of the formula (I), by reaction with trifluoromethanesulphonyl chloride or trifluoromethanesulphonic anhydride, optionally in the presence of a suitable acid acceptor, e.g. triethylamine, pyridine or potassium carbonate. The reaction is typically carried out in a suitable organic solvent, e.g. dichloromethane or acetonitrile;

(d) a compound of the formula (I) wherein W is $NSO_2(C_1-C_4\text{ alkyl})$, $NSO_2NR^5R^6$, $NSO_2$ (morpholino), $NSO_2$(piperidino), $NSO_2$(aryl), $CHNR^5(SO_2\ C_1-C_4\text{ alkyl})$ or $CHNR^5SO_2NR^5R^6$, $W^1$ is $CHNR^5(SO_2\ C_1-C_4\text{ alkyl})$ or $CHNR^5SO_2NR^5R^6$, or $R^9$ is $-NR^5(SO_2\ C_1-C_4\text{ alkyl})$ or $-NR^5SO_2NR^5R^6$, as appropriate, wherein $R^5$ and $R^6$ are as previously defined for a compound of the formula (I), by reaction with a $C_1-C_4$ alkanesulphonyl chloride or bromide, a $C_1-C_4$ alkanesulphonic anhydride or a compound of the formula:

$R^5R^6NSO_2(Cl\text{ or }Br)$, (morpholino)$SO_2(Cl\text{ or }Br)$, (piperidino)$SO_2(Cl\text{ or }Br)$, or (aryl)$SO_2(Cl\text{ or }Br)$, as appropriate, optionally in the presence of a suitable acid acceptor, e.g. triethylamine.

The reaction is typically carried out in a suitable organic solvent, e.g. dichloromethane, at from 0° C. to room temperature;

(e) a compound of the formula (I) wherein W is $NCOR^6$ or $CHNR^5COR^6$, $W^1$ is $CHNR^5COR^6$ or $R^9$ is $-NR^5COR^6$, as appropriate, wherein $R^5$ and $R^6$ are as previously defined for a compound of the formula (I) with the proviso that $R^6$ is not H, by reaction with a compound of the formula:

$R^6CO(Cl\text{ or }Br)$ or $(R^6CO)_2O$ wherein $R^6$ is as previously defined for this Method, optionally in the presence of a suitable acid acceptor, e.g. triethylamine. The reaction is typically carried out in a suitable organic solvent, e.g. dichloromethane, at from 0° C. to room temperature;

(f) a compound of the formula (I) wherein W, $W^1$ or $R^9$ is as previously defined for Method 10(e), as appropriate, by condensation with a compound of the formula:

$R^6CO_2H$ wherein $R^6$ is as previously defined for this Method. The reaction can be performed under conventional conditions, e.g. using 1,1'-carbonyldiimidazole or 1-hydroxybenzotriazole/1,3-dicyclohexylcarbodiimide to generate activated intermediates;

(g) a compound of the formula (I) where W is $NSO_2NR^5R^6$ or $CHNR^5SO_2NR^5R^6$, $W^1$ is $CHNR^5SO_2NR^5R^6$ or $R^9$ is $-NR^5SO_2NR^5R^6$, as appropriate, wherein $R^5$ and $R^6$ are as previously defined for a compound of the formula (I), by reaction with a compound of the formula:

$R^5R^6NSO_2NH_2$

The reaction is typically carried out at an elevated temperature in a suitable solvent, e.g. 1,4-dioxane.

11) The compounds of the formula (I) wherein $R^2$ is:

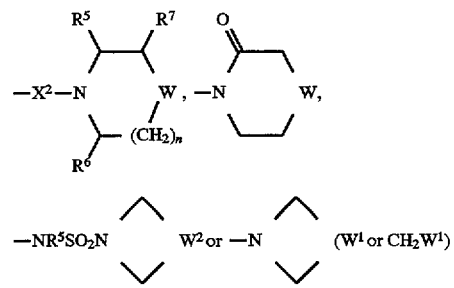

wherein W and $W^1$ are $CHCO_2H$ and $W^2$ is $W^1$, $-CH_2W^1-$, $-CH_2WCH_2-$ or $-CH_2CH_2WCH_2-$ and X, $X^1$, $X^2$, R, $R^1$, $R^2$, $R^5$, $R^6$, $R^7$ and n are as previously defined for a compound of the formula (I), may be prepared by hydrolysis of a compound of the formula (I) wherein W and $W^1$ are $CHCO_2(C_1-C_4\text{ alkyl})$, $W^2$ is $W^1$, $-CH_2W^1$, $-CH_2WCH_2-$ or $-CH_2CH_2WCH_2-$ and X, $X^1$, $X^2$, R, $R^1$, $R^2$, $R^5$, $R^6$, $R^7$ and n are as previously defined for a compound of the formula (I). Preferably, W and $W^1$ are $CHCO_2CH_3$ or $CH_2CO_2CH_2CH_3$.

The hydrolysis is typically carried out using an aqueous solution of a suitable acid or base, e.g. a mineral acid such as hydrochloric or sulphuric acid or a base such as sodium or potassium hydroxide, optionally in the presence of a suitable organic co-solvent, e.g. methanol or ethanol.

12) The compounds of the formula (I) wherein $R^2$ is

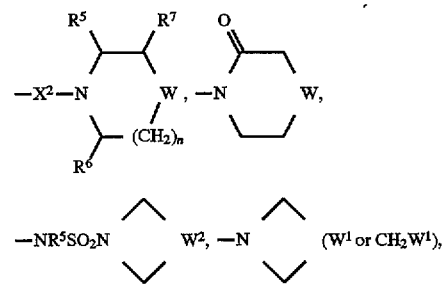

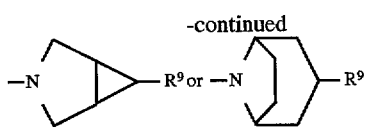

wherein W and W¹ are CHNR⁵R⁶, W² is W¹, —CH₂W¹—, —CH₂WCH₂— or —CH₂CH₂WCH₂—, R⁹ is —NR⁵R⁶ and X, X¹, X², R, R¹, R², R⁵, R⁶, R⁷ and n are as previously defined for a compound of the formula (I) may be prepared by reaction of a compound of the formula (XIII):

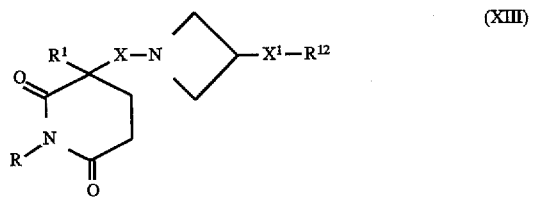

wherein R¹² is

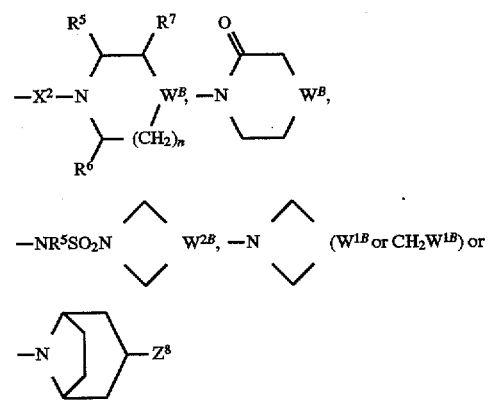

wherein $W^B$ and $W^{1B}$ are $CHZ^8$, $W^{2B}$ is $W^{1B}$, —CH₂W^{1B}—, —CH₂W^BCH₂— or —CH₂CH₂W^8CH₂—, $Z^8$ is a suitable leaving group, e.g. halo, (preferably chloro or bromo), methanesulphonyloxy, trifluoromethanesulphonyloxy or p-toluenesulphonyloxy, and X, X¹, X², R, R¹, R⁵, R⁶, R⁷ and n are as previously defined for a compound of the formula (I), with a compound of the formula:

HNR⁵R⁶ wherein R⁵ and R⁶ are as previously defined for a compound of the formula (I), optionally in the presence of a suitable additional acid acceptor, e.g. triethylamine or potassium carbonate.

The reaction is typically carried out in a suitable solvent such as acetonitrile.

13) The compounds of the formula (I) wherein R² is

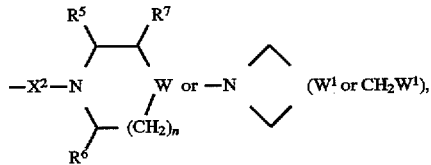

W and W¹ are CHNR⁵R⁶ and X, X¹, X², R, R¹, R⁵, R⁶, R⁷ and n are previously defined for a compound of the formula (I), may be prepared by reductive amination using as the starting materials a compound of the formula (I): wherein R² is

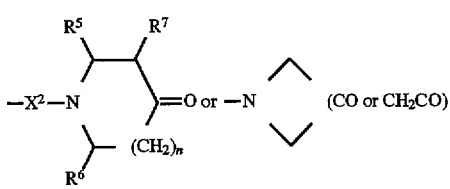

and X, X¹, X², R, R¹, R⁵, R⁶, R⁷ and n are as previously defined for a compound of the formula (I), and a compound of the formula:

HNR⁵R⁶ wherein R⁵ and R⁶ are as previously defined for a compound of the formula (I).

Conventional conditions are used such as those described for Method (1). Again, the intermediate imine or iminium species formed may be stable or isolatable. The reaction is preferably carried out without isolation of this intermediate in which case it is reduced in situ to provide a compound of the formula (I).

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of formula (I) and their salts for the human $NK_1$ receptor can be tested in vitro by testing their ability to inhibit [³H]-Substance P binding to membranes prepared from the human IM9 cell line expressing the human $NK_1$ receptor using a modification of the method described in McLean, S. et al, J. Pharm. Exp. Ther., 267, 472–9 (1993) in which whole cells were used.

The affinity of the compounds of formula (I) and their salts for the human $NK_2$ receptor can be tested in vitro by testing their ability to compete with [³H] or [²⁵¹I]NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [³H] or [¹²⁵I] NKA and with a range of concentrations of the test compound. Non-specific binding was determined in the presence of 10μM NKA.

The $NK_2$ receptor antagonist activity of the compounds of the formula (I) can be tested, in vitro, by testing their ability to antagonise the contractile effects of the selective $NK_2$ receptor agonist [βAla⁸]NKA$_{(4-10)}$ in the rabbit pulmonary artery, using the method of Patacchini and Maggi, Eur. J. Pharmacol., 236, 31–37 (1993).

The compounds of the formula (I) and their salts can be tested for $NK_2$ receptor antagonist activity, in vivo, by testing their ability to inhibit bronchoconstriction induced by [βAla⁸]NKA$_{(4-10)}$ in the anaesthetised guinea pig, using the method described by Murai et al, J. Pharm. Exp. Ther., 262,403–408 (1992) or Metcalfe et al, Br. J. Pharmacol., 112, 563P (1994).

The compounds of the formula (I) and their salts can be tested for $NK_3$ receptor antagonist activity, in vitro, by testing their ability to antagonise the contractile effects of the selective $NK_3$ receptor agonist senktide in the guinea-pig ileum using the method of Maggi et al, Br. J. Pharmacol., 101, 996–1000 (1990).

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.1 to 10, and most preferably from 0.5 to 5, mg/kg (in single or divided doses). Thus tablets or capsules of the compounds will contain from 0.1 to 500, preferably from 50 to 200, mg of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect on a tachykinin acting at the human $NK_1$, $NK_2$ or $NK_3$ receptor, or a combination of two or more thereof;

iv) use as in (iii) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain;

v) a method of treatment of a human to treat a disease by producing an antagonist effect on a tachykinin acting at the human $NK_1$, $NK_2$ or $NK_3$ receptor, or a combination of two or more thereof, which comprises treating said human with an effective amount of a compound of the formula (I) or with a pharmaceutically acceptable salt or composition thereof;

vi) a method as in (v) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain; and vii) a compound of the formula (II), (IIIA), (V), (VI), (VII), (VIII), (VIIIa), (IX), (X), (XI), (XII) and (XIII).

The following Examples illustrate the preparation of the compounds of the formula (I):

EXAMPLE 1

1-Cyclohexylmethyl-3-(3,4-dichlorophenyl)-3-(2-(3-morpholinoazetidin-1-yl)ethyl)glutarimide

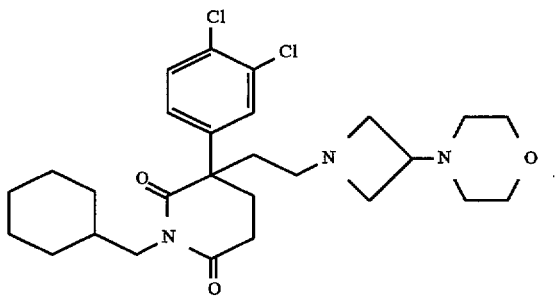

1(a) 2-(3,4-Dichlorophenyl)pent-4-enenitrile

To a stirred solution of 3,4-dichlorophenylacetonitrile (800 g, 4.3 mol) in cyclohexane (16 l) at room temperature was carefully added aqueous NaOH solution (1.6 kg NaOH in 8 l of water). The addition caused the temperature of the reaction to increase to 50° C. Allyl bromide (572 g, 1.1 mol equivalents) and tetra-n-butylammonium chloride hydrate (40 g, 0.03 mol equivalents) were then added and the reaction was stirred for 1 hr at 50° C. The aqueous phase was then separated and the organic layer washed with water (10 l), then filtered through silica gel (1 kg) under reduced pressure to give a yellow filtrate solution. Removal of the solvent from said filtrate in vacuo gave the title compound as an oil (960 g) of 70% purity, which was used without further purification. TLC $R_f=0.71$ (silica, diethyl ether:hexane, 1:1).

LRMS m/z=226 (m)⁺.

¹H NMR (CDCl₃): 2.6–2.75 (m, 2H); 3.85 (t, 1H); 5.1–5.25 (m, 2H); 5.7–5.9 (m,1H), 7.2–7.25 (m, 1H), 7.5–7.55 (m, 2H) ppm.

1(b) 4-Cyano-4-(3,4-dichlorophenyl)hept-6-enoic acid

To a stirred suspension of 60% w/w NaH oil dispersion (231 g) in tetrahydrofuran (THF) (17l) under nitrogen at −10° C. was added a solution of 3-bromopropanoic acid (806.5 g) in THF dropwise over 3 hours. The reaction was allowed to warm to room temperature over 22 hours, and then cooled to −10° C. Simultaneously, a solution of the compound from 1(a) above (1633.5 g)in THF (2.5 l) was added dropwise over 2 hours to a stirred suspension of 60% w/w NaH oil dispersion (221 g) in THF (2.5 l) under nitrogen at −10° C. When the addition was complete, this second reaction was allowed to warm to room temperature over 18 hours. The reaction was then cooled to −10° C. and cannulated into the above 3-bromopropanoic acid sodium salt mixture over 3 hours. The reaction mixture was heated to 50° C. for 5 hours, then cooled, poured into water (8 l) and basified to pH 9.3 using aqueous NaHCO₃ solution. This mixture was washed with dichloromethane (5×2 l) and the aqueous portion acidified to pH 1.0 using concentrated HCl. The aqueous solution was extracted with dichloromethane (4×2.5 l) and the organic layers were combined, dried using anhydrous MgSO₄, filtered and the filtrate concentrated in vacuo to give a yellow oil. This oil was then triturated with hexane (1.5 l) to give the title compound as a cream solid (1155.3 g) which was used without any further purification.

TLC $R_f=0.42$ (silica, methanol:dichloromethane 1:9).

LRMS m/z=316 (m+NH₄)⁺.

¹H NMR (CDCl₃): 2.15–2.8 (m, 6H); 5.1–5.25 (m, 2H); 5.55–5.7 (m, 1H); 7.2–7.25 (m, 1H); 7.5–7.55 (m, 2H) ppm.

1(c) 3-Allyl-3-(3,4-dichlorophenyl)-(1H)-glutarimide

A solution of the compound from 1(b) above (10 g), formic acid (12 ml) and concentrated HCl (6 ml) in N,N-dimethylformamide (DMF) (69 ml) was heated at 145° C. for 48 hours.

The solution was cooled to room temperature and water (100 ml) was added. The mixture was basified with 15% aqueous Na₂CO₃ solution until an oily precipitate formed, and then extracted with ethyl acetate (2×100 ml). The combined organic phases were then dried over anhydrous Na₂SO₄, filtered and the solvent removed in vacuo to give an oil, which was purified by flash chromatography (silica, ethyl acetate) to give the title compound (4.3 g).

LRMS m/z 298 (m+1)⁺.

¹H NMR (d⁶-DMSO): 2.1–2.2 (m, 2H); 2.3–2.7 (m, 4H); 5.0–5.1 (m, 2H); 5.5–5.7 (m, 1H); 7.2–7.6 (m, 3H); 10.95 (s, br, 1H) ppm.

1(d) 3-Allyl-1-cyclohexylmethyl-3-(3,4-dichlorophenyl) glutarimide

To a mixture of NaH (80 mg, 60% dispersion in oil) in DMF (10 ml), cooled in an ice-bath under nitrogen, was added the compound of 1(c) above (0.5 g) and the mixture was stirred for 45 minutes. Cyclohexylmethyl bromide (0.26 ml) was then added and the reaction mixture was heated to 50° C. for 18 hours. The reaction was cooled to room temperature and the solvent was removed in vacuo. Water (20 ml) was added and the mixture extracted with ethyl acetate (2×20 ml). The combined organics were washed with brine (40 ml) and dried over anhydrous Na₂SO₄. The solution was then filtered, and the solvent removed in vacuo to give an oil which was purified by flash chromatography (silica, diethyl ether:hexane 1:4) to give the title compound.

TLC $R_f=0.46$ (silica, diethyl ether: hexane, 1:1).

LRMS m/z=394 (m+1)⁺.

¹H NMR (CDCl₃): 0.9–1.1 (m, 2H); 1.15–1.3 (m, 3H); 1.4–1.75 (m, 6H); 2.15–2.8 (m, 6H); 3.7 (d, 2H); 5.0–5.15 (m, 2H); 5.55–5.65 (m, 1H); 7.1–7.4 (m, 3H) ppm.

1(e) 1-Cyclohexylmethyl-3-(3,4-dichlorophenyl)-3-formylmethylglutarimide

Into a solution of the compound of 1(d) above (0.45 g) in methanol (25 ml) under nitrogen at −78° C. was bubbled ozone at rate of 50 ml/minute (using a charge of 1.5A to generate ozone from oxygen) for 20 minutes. The current was then reduced to zero, and oxygen was bubbled through the reaction at a rate of 5 ml/minute for 10 minutes. The oxygen supply was then removed and a solution of dimethyl sulphide (DMS) (0.83 ml) in methanol (3 ml) was added dropwise, and the reaction was left to warm to room temperature for 18 hours. The solvent was removed in vacuo and the mixture was partitioned between ethyl acetate (20 ml) and water (20 ml). The organic layer was then dried over anhydrous MgSO₄, filtered and the solvent removed in vacuo to give a residue which was purified by flash chromatography (silica, diethyl ether: hexane, 1:1) to give the title compound (0.265 g).

LRMS m/z =396 m+1)⁺.

¹H NMR (CDCl₃): 0.95–1.3 (m, 5H); 1.5–1.8 (m, 6H); 2.2–2.4 (m, 2H); 2.55–2.85 (m, 3H); 3.2 (d, 1H); 3.75 (d, 2H); 7.05–7.5 (m, 3H); 9.6 (s, 1H) ppm.

1(f) 1-Cyclohexylmethyl-3-(3,4-dichlorophenyl)-3-(2-(3-morpholinoazetidin-1-yl)ethyl)glutarimide To a solution of the aldehyde product of 1(e) above (0.23 g) and 3-morpholinoazetidine dihydrochloride (0.14 g) (Preparation 1 ) in THF (30 ml) under nitrogen was added triethylamine (0.25 g). After 90 minutes, sodium triacetoxyborohydride (0.16 g) was added, followed immediately by glacial acetic acid (0.09 ml), and the mixture was stirred for 18 hours. Saturated aqueous NaHCO₃ solution (10 ml) was then added and the mixture extracted with ethyl acetate (2×20 ml). The combined organic layers were washed with water (50 ml) and dried over anhydrous MgSO₄. The solution was filtered, the solvent removed in vacuo and the residue purified by column chromatography (silica, dichloromethane:methanol, 19:1) to give the title compound (0.273 g).

TLC $R_f=0.16$ (silica, dichloromethane:methanol, 19:1).

LRMS m/z=522 (m+1)⁺.

¹H NMR (CDCl₃): 0.95–1.3 (m, 5H); 1.5–1.8 (m, 6H); 1.85–2.1 (m, 2H); 2.1–3.0 (m, 13H); 3.4–3.5 (m, 2H), 3.7–3.75 (m, 6H); 7.1–7.45 (m, 3H) ppm.

EXAMPLE 2

3(S)-1-Cyclohexylmethyl-3-(3,4-dichlorophenyl)-3-(2-(3-morpholinoazetidin-1-yl)ethyl)glutarimide

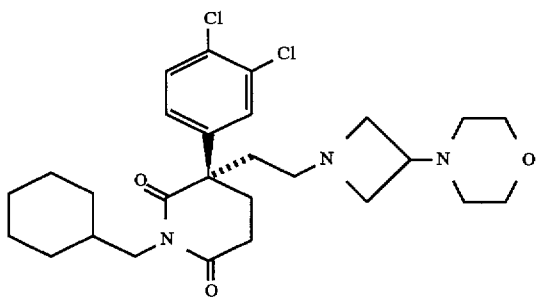

2(a) 4(S)-4-Cyano-4-(3,4-dichlorophenyl)hept-6-enoic acid
(i) R-(+)-1-(1-naphthyl)ethylamine salt To a solution of the compound of Example 1(b) above (16 g) in ethyl acetate (50 ml) was added R-(+)-1-(1-naphthyl) ethylamine (4.8 g). The solution was stirred for 30 minutes at room temperature and then the solvent removed in vacuo to give a gum. This was partially dissolved in hexane: diethyl ether (4:1, 150 ml) and the sides of the flask scratched to induce crystallisation. The white solid that formed was filtered off and crystallised 3 times from ethyl acetate to give the title compound (4.9 g).

m.p. 153°–4° C.

$[\alpha]_{589}$=–7.1° (25° C., c=0.0012).

$^1$H NMR (CDCl$_3$): 1.6 (d,3H); 2.0–2.2 (m, 2H); 2.25–2.5 (m, 2H); 2.5–2.7 (m, 2H); 3.8–4.1 (s, br, 3H); 5.0–5.2 (m, 3H); 5.5–5.7 (m, 1H); 7.15–7.25 (m, 1H); 7.4–7.6 (m, 6H); 7.75 (d, 1H); 7.9 (d, 1H); 8.1 (d, 1H) ppm.

(ii) Free Acid

To a stirred solution of the R-(+)-1-(1-naphthyl) ethylamine salt from (i) above (5.5 g) in dichloromethane (100 ml) was added 1N aqueous HCl (100 ml). The aqueous layer was then removed and the organic portion washed with 1N aqueous HCl (70 ml). The organic layer was dried over MgSO$_4$, filtered and the filtrate reduced in vacuo to give the title compound (3.6 g).

LRMS m/z=316 (m+NH$_4$)$^+$.

$^1$H NMR (CDCl$_3$): 2.15–2.8 (m, 6H); 5.1–5.25 (m, 2H); 5.55–5.7 (m, 1H); 7.2–7.25 (m, 1H); 7.5–7.55 (m, 2H) ppm.

2(b) 3(S)-Allyl-3-(3,4-dichlorophenyl)-(1H)-glutarimide

This compound was made in the same way as described in Example 1(c) above, using the chiral acid of Example 2(a)(ii) above.

TLC R$_f$=0.87 (silica, ethyl acetate: hexane, 1:3).

m.p. 137°–8° C.

$[\alpha]_{589}$=178° (25° C., c=0.00034).

$^1$H NMR (CDCl$_3$): 2.1–2.7 (m, 6H); 5.1–5.2 (m, 2H); 5.55–5.65 (m, 1H); 7.2–7.6 (m, 3H) ppm.

2(c) 3(S)-3-Allyl-1-cyclohexylmethyl-3-(3,4-dichlorophenyl)-glutarimide

This was made in the same way as described in Example 1(d) above, using the chiral glutarimide of Example 2(b) above.

LRMS and $^1$H NMR data corresponded with that of Example 1(d) above.

2(d) 3(S)-1-Cyclohexylmethyl-3-(3,4-dichlorophenyl)-3-formylmethylglutarimide

This was made in the same way as described in Example 1(e) above, using the chiral glutarimide of Example 2(c) above.

LRMS and $^1$H NMR data corresponded with that of Example 1(e) above.

2(e) 3(S)-1-Cyclohexylmethyl-3-(3,4-dichlorophenyl)-3-(2-(3-morpholinoazetidin-1-yl)ethyl)glutarimide This was made by the same method to that described above in 1(f), Using the chiral aldehyde of 2(d) above.

LRMS m/z=522 (m+1)$^+$.

Found: C 60.98%; H 7.40%; N 7.43 %. C$_{27}$H$_{37}$Cl$_2$N$_3$O$_3$.0.5H$_2$O requires C 61.0%; H 7.03%; N 7.90%.

$^1$H NMR (CDCl$_3$): 0.95–1.3 (m, 5H); 1.5–1.8 (m, 6H); 1.85–2.1 (m, 2H); 2.1–3.0 (m, 13H), 3.4–3.5 (m, 2H); 3.7–3.75 (m, 6H); 7.1–7.45 (m, 3H) ppm.

$[\alpha]_{589}$=90.4° (25° C., c =0.00022).

EXAMPLE 3

3(S)-3-(2-(3-(4-Aminosulphonylpiperazin-1-yl)azetidin-1-yl)ethyl)-1-cyclohexylmethyl-3-(3,4-dichlorophenyl) glutarimide

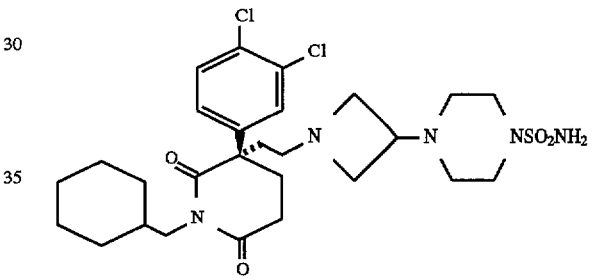

This was made in the same way as described in Example 2(e) above, using 3-(4-aminosulphonylpiperazin-1-yl) azetidine bistrifluoroacetate (Preparation 2).

LRMS m/z=600 (m+1)$^+$.

$^1$H NMR (CDCl$_3$): 0.9–1.3 (m, 5H); 1.4–1.8 (m, 7H); 1.85–2.15 (m, 2H); 2.2–2.5 (m, 8H); 2.55–2.7 (m, 1H); 2.85–3.1 (m, 3H), 3.2–3.25 (m, 4H); 3.4–3.5 (m, 2H); 3.7–3.75 (m, 2H); 4.3 (s, br, 2H); 7.05–7.45 (m, 3H) ppm.

EXAMPLE 4

3(S)-1-Cyclopropylmethyl-3-(3,4-dichlorophenyl)-3-(2-(3-(4-morpholinosulphonylpiperazin-1-yl)azetidin-1-yl)ethyl) glutarimide

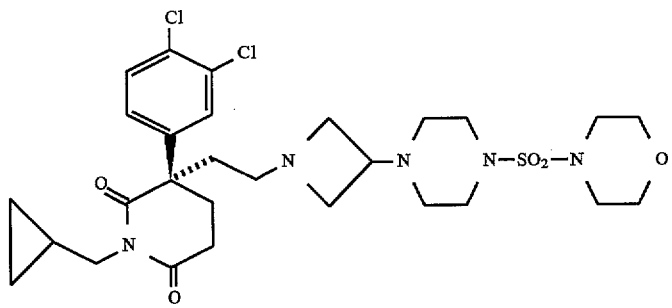

4(a) 3(S)-3-Allyl-1-cyclopropylmethyl-3-(3,4-dichlorophenyl)glutarimide

This was made in the same way as that described in Example 2(c) above, using cyclopropylmethyl bromide.

LRMS m/z=352 (m+1)$^+$.

$^1$H NMR (CDCl$_3$): 0.3–0.55 (m,4H); 0.95–1.1 (m,1 H); 2.2–2.9 (m,6H); 3.3 (d,2H); 5.05–5.2 (m,2H); 5.6–5.75 (m,1H); 7.1–7.45 (m,3H) ppm.

4(b) 1-Cyclopropylmethyl-3-(3,4-dichlorophenyl)-3-formylmethylglutarimide

This was made in the same way as that described in Example 2(d) above, using the compound of Example 4(a) above.

LRMS m/z=354 (m+1)$^+$.

$^1$H NMR (CDCl$_3$): 0.3–0.55 (m, 4H); 1.15–1.3 (m, 1H); 1.8–1.9 (m, 1H); 2.2–2.4 (m, 3H); 2.55–2.85 (m, 3H); 3.2–3.3 (m, 1H); 7.1–7.5 (m, 3H), 9.65 (s, 1H) ppm.

4(c) 3(S)-1-Cyclopropylmethyl-3-(3,4-dichlorophenyl)-3-(2-(3-(4-morpholinosulphonlpiperazin-1-yl)azetidin-1-yl)ethyl)glutarimide This was made in the same way as described in Example 1(f) above using the chiral aldehyde of Example 4(b) above and 3-(4-morpholinosulphonylpiperazin-1-yl)azetidine bis-trifluoroacetate (Preparation 3).

LRMS m/z=628 (m+1)$^+$.

Found: C 52.8%; H 6.02%; N 11.01 %. C$_{28}$H$_{39}$Cl$_2$N$_5$O$_5$S.0.5H$_2$O requires C52.74%; H 6.34%; N 10.99%.

$^1$H NMR (CDCl$_3$): 0.3–0.6 (m,3H); 1.1–1.25 (m,2H); 1.8–1.95 (m,1H); 2.0–2.1 (m,1H); 2.15–2.45 (m,8H); 2.5–2.75 (m,2H); 2.75–2.8 (m,2H); 2.9–3.0 (m,1H); 3.2–3.4 (m,8H); 3.4–3.45 (m,2H); 3.65–3.8 (m,6H); 7.05–7.1 (m,1H); 7.3–7.35 (m,1H); 7.4–7.45 (m,1H) ppm.

Examples 5–7 were made in the same way as described in Example 4(c) above, using the appropriate amine or amine salt (see Preparations).

EXAMPLE 5

3(S)-3-(2-(3-(4-Aminosulphonylpiperazin-1-yl)azetidin-1-yl)ethyl)-1-cyclopropylmethyl-3-(3,4-dichlorophenyl)glutarimide

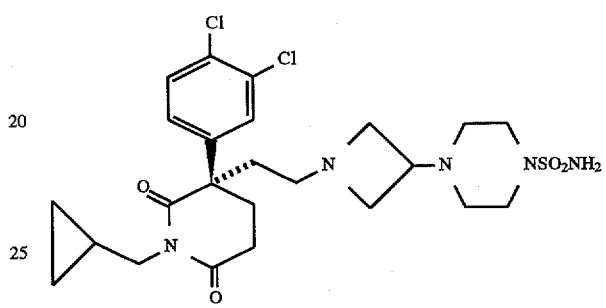

LRMS m/z=558 (m)$^+$.

Found: C 51.09%; H 5.62%; N 11.87 %. C$_{24}$H$_{33}$Cl$_2$N$_5$O$_4$S. 0.5H$_2$O requires C 50.79%; H 6.05%; N 12.34%.

$^1$H NMR (CDCl$_3$): 0.3–0.6 (m, 4H); 1.1–1.3 (m, 1H); 1.8–2.0 (m, 1H); 2.0–2.1 (m, 1H); 2.2–2.4 (m, 8H); 2.4–2.55 (m, 1H); 2.8–3.05 (m, 4H); 3.2–3.4 (m, 6H); 3.6–3.9 (m, 2H); 4.2–4.4 (m, 2H); 7.0–7.05 (m, 1H); 7.35–7.45 (m, 2H) ppm.

EXAMPLE 6

3(S)-1-Cyclopropylmethyl-3-(3,4-dichlorophenyl)-3-(2-(3-(4-dimethylaminosulphonylpiperazin-1-yl)azetidin-1-yl)ethyl)glutarimide

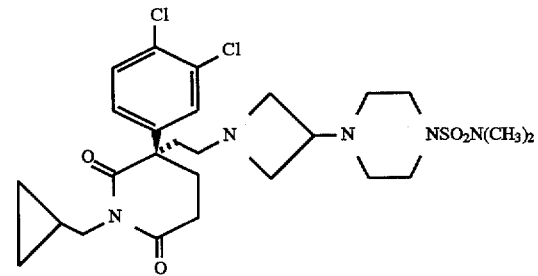

LRMS m/z=586 (m)$^+$.

Found: C 52.43%; H 6.44%; N 11.75 %. C$_{26}$H$_{37}$Cl$_2$N$_5$OS. 0.5H$_2$O requires C 52.14%; H 6.07%; N 11.53%.

$^1$H NMR (CDCl$_3$): 0.3–0.6 (m, 4H); 1.1–1.2 (m, 1H); 1.6–1.8 (m, 2H); 1.8–1.95 (m, 1H); 2.0–2.2 (m, 1H); 2.2–2.4 (m, 8H); 2.5–2.8 (m, 2H); 2.8–3.0 (m, 7H); 3.2–3.4 (m, 4H); 3.4–3.6 (m, 2H); 3.7–3.9 (m, 2H); 7.05–7.15 (m, 1H); 7.3–7.5 (m, 2H) ppm.

EXAMPLE 7

3(S)-1-Cyclopropylmethyl-3-(3,4-dichlorophenyl)-3-(2-(3-(4-piperidinosulphonylpiperazin-1-yl)azetidin-1-yl)ethyl)glutarimide

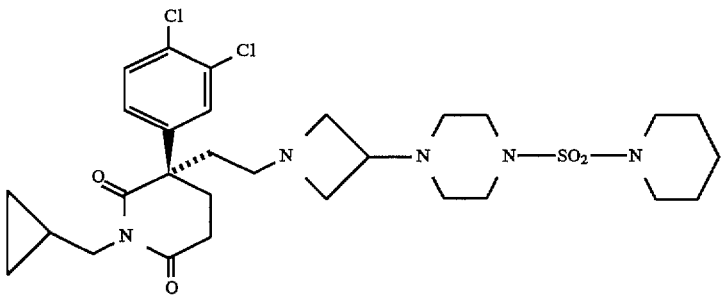

LRMS m/z=626 (m)⁺.
Found: C 64.62%; H 6.72%; N 10.98 %. $C_{29}H_{41}Cl_2N_5O_4S$. 0.5$H_2O$ requires C 54.79%; H 6.67%; N 11.02%.

¹H NMR (CDCl₃): 0.3–0.6 (m, 4H); 1.1–1.2 (m, 1H); 1.8–1.95 (m, 1H); 2.1–2.25 (m, 11H); 2.5–2.7 (m, 3H); 2.8–3.0 (m, 3H); 3.2–3.4 (m, 11H); 3.4–3.6 (m, 2H); 3.6–3.85 (m, 2H); 7.05–7.1 (m, 1H); 7.3–7.5 (m, 2H) ppm.

EXAMPLE 8
3(S)-3-(2-(3-(4-Aminosulphonylpiperazin-1-yl)azetidin-1-yl)ethyl)-1-cyclopropylethyl-3-(3,4-dichlorophenyl)glutarimide

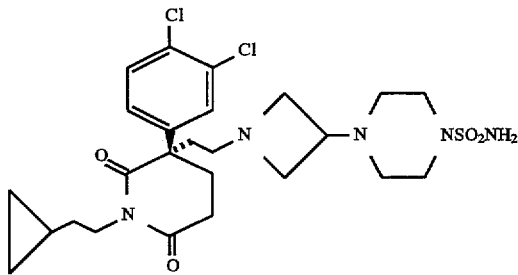

8(a) 3(S)-3-Allyl-1-cyclopropylethyl-3-(3,4-dichlorophenyl)-glutarimide

This was made by the same method as described in Example 1(d) above, using the compound of Example 2(b) and 2-methanesulphonyloxyethylcyclopropane (Preparation 5).

LRMS m/z=366 (m+1)⁺.

¹H NMR (CDCl₃): 0.0–0.1 (m, 2H); 0.4–0.45 (m, 2H); 0.6–0.7 (m, 1H); 0.8–0.9 (m, 2H); 2.1–2.8 (m, 6H); 3.9–3.95 (m, 2H); 5.1–5.15 (m, 2H); 5.5–5.65 (m, 1H); 7.1–7.4 (m, 3H) ppm.

8(b) 3(S)-1-(2-cyclopropylethyl)-3-(3,4-dichlorophenyl)-3-formylmethylglutarimide This was made by the same method as described above in Example 1(e), using the compound of Example 8(a).

LRMS m/z=368 (m+1)⁺.

¹H NMR (CDCl₃): 0.05–0.15 (m,2H); 0.4–0.45 (m,2H); 0.65–0.75 (m,1 H); 1.45–1.55 (m,2H); 2.1–2.45 (m,3H); 2.55–2.65 (m,2H); 2.8–2.9 (m,1H); 3.9–4.05 (m,2H); 7.05–7.45 (m,3H); 9.65 (s,1H) ppm.

8(c) 3(S)-3-(2-(3-(4-Aminosulphonylpiperazin-1-yl)azetidin-1-yl)ethyl)-1-cyclopropylethyl-3-(3,4-dichlorophenyl)glutarimide This was made by the same method as described above in Example 1(f), using the compound of Example 8(b) and 3-(4-aminosulphonylpiperazin-1-yl)azetidine bistrifluoroacetate (Preparation 2).

LRMS m/z=547 (m+1)⁺.
Found: C 51.22%; H 5.78%; N 11.49 %. $C_{25}H_{35}Cl_2N_5O_4S$. 0.25 $CH_2Cl_2$ requires C 51.17%; H 6.04%; N 11.32%.

¹H NMR (CDCl₃):0.0–0.1 (m, 2H); 0.3–0.45 (m, 2H); 0.6–0.7 (m, 1H); 1.4–1.55 (m, 2H); 1.8–1.9 (m, 1H); 1.9–2.0 (m, 1H); 2.1–2.6 (m, 10H); 2.7–2.8 (m, 2H); 2.85–2.95 (m, 1H); 3.1–3.3 (m, 4H); 3.4–3.55 (m, 2H); 3.8–4.0 (m, 2H); 4.4–4.6 (m, 2H); 7.0–7.05 (m, 1H); 7.2–7.3 (m, 1H); 7.3–7.4 (m, 1H) ppm.

EXAMPLE 9
3(S)-1-Cyclopropylethyl-3-(3,4-dichlorophenyl)-3-(2-(3-(4-morpholinosulphonylpiperazin-1-yl)azetidin-1-yl)ethyl)glutarimide

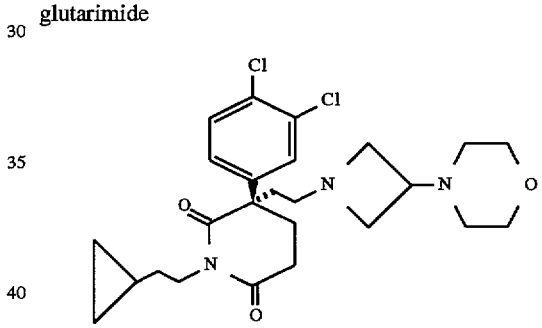

This was made by the same method as described above in Example 1(f), using the aldehyde of Example 8(b) and 3-morpholinoazetidine dihydrochloride (Preparation 1).

LRMS m/z=494 (m)⁺.
Found: C 57.08%; H 6.52%; N 7.83%. $C_{25}H_{33}Cl_2N_3O_2$. 0.5 $CH_2Cl_2$ requires C 57.04%; H 6.38%; N 7.83%.

¹H NMR (CDCl₃): 0.0–0.1 (m, 2H); 0.4–0.6 (m, 2H); 0.6–0.8 (m, 1H); 1.3–1.5 (m, 2H); 1.8–1.95 (m,1H); 1.95–2.05 (m, 1H); 2.1–2.75 (m, 9H); 2.8–3.0 (m, 4H); 3.4–3.5 (m, 2H); 3.6–3.75 (m, 4H); 3.8–4.0 (m, 2H); 7.0–7.05 (m, 1H); 7.25–7.4 (m, 2H) ppm.

The following Preparations illustrate the synthesis of certain starting materials used in the preceding Examples.

PREPARATIONS
PREPARATION 1,3-Morpholinoazetidine dihydrochloride
1(a) 1-Diphenylmethylazetidin-3-ol A solution of benzhydrylamine (200 ml, 1.16 mol) and epichlorohydrin (186 ml, 1 mol equiv) in methanol (600 ml) was stirred at room temperature for 5 days and then heated to 40° C. for 2 days. The solvent was then removed in vacuo, the residue dissolved in isopropyl alcohol (500 ml) and the solution heated under reflux for 6 hours. The solution was cooled to room temperature and the precipitate filtered off. The solid was partitioned between dichloromethane (400 ml) and saturated NaHCO₃ solution (500 ml). The aqueous phase was extracted with dichloromethane (2×400 ml) and the combined organic phases dried over anhydrous MgSO₄. The solvent was then removed in vacuo to give the title compound (86 g) as a crystalline solid.

¹H NMR (CDCl₃): 1.8–2.3 (s,br, 1H); 2.85–2.9 (m,2H); 3.5–3.55 (m,2H); 4.35 (s,1H); 4.4–4.5 (m,1H); 7.15–7.4 (m, 10H) ppm.

1(b) 1-Diphenylmethyl-3-methanesulphonyloxyazetidine

To a solution of the compound from Preparation 1(a) (65.9 g, 275.7 mmol) in dry dichloromethane (700 ml) at 0° C. under nitrogen was added triethylamine (57 ml, 1.5 mol eq). After 5 minutes, methanesulphonyl chloride (25.6 ml, 1.2 mol equiv) was added and the mixture stirred for 1 hour. Water (300 ml) was then added and the mixture extracted with dichloromethane (3×300 ml). The combined organic layers were dried over MgSO₄, and the solvent was then removed in vacuo. The residue was chromatographed using silica gel eluting with methanol:dichloromethane (1:49) to give the title compound (73.4 g) as a solid.

¹H NMR (CDCl₃): 2.95 (s,3H); 3.15–3.25 (m, 2H); 3.6–3.65 (m, 2H); 4.4 (s, 1H); 5.05–5.15 (m,1H); 7.15–7.4 (m,10H) ppm.

1(c) 1-Diphenylmethyl-3-morpholinoazetidine

A solution of 1-diphenylmethyl-3-methanesulphonyloxyazetidine (Preparation 1(b)) (24.46 g, 7.72 mmol), potassium carbonate (32 g, 3 mol equiv) and morpholine (7.34 ml, 1.09 mol equiv) in acetonitrile (200 ml) was heated under reflux for 4 hours. The solution was then cooled to room temperature, water (50 ml) added and the mixture concentrated in vacuo. The residue was then partitioned between ethyl acetate (400 ml) and water (400 ml) and the organic phase washed with water (2×400 ml). The organic phase was dried over MgSO₄, and the solvent removed in vacuo. The residue was chromatographed using silica gel eluting with hexane: diethyl ether (1:1) to give the title compound (16.5 g).

¹H NMR (CDCl₃): 2.25–2.3 (m,4H); 2.85–3.05 (m,3H); 3.35–3.4 (m,2H); 3.7–3.75 (m,4H); 4.45 (s,1H); 7.15–7.45 (m,10H) ppm.

1(d) 3-Morpholinoazetidine dihydrochloride

A mixture of 1-diphenylmethyl-3-morpholinoazetidine (Preparation 1(c)) (18.6 g, 60.4 mmol), palladium hydroxide (2 g), ethanol (200 ml) and 1N aqueous HCl (52 ml) was stirred under an atmosphere of hydrogen at 345 kPa (50p.s.i.) for 3 days. The catalyst was then removed by filtration and the filtrate evaporated to dryness. Addition of dichloromethane (100 ml) to the residue and trituration gave a solid which was recrystallised from methanol to give the title compound (10.2 g) as a crystalline solid. LRMS m/z= 179 (m+1)⁺.

PREPARATION 2,3-(4-Aminosulphonylpiperazin-1-yl) azetidine bistrifluoroacetate

2(a) 1-(t-Butoxycarbonyl)-3-(piperazin-1-yl)azetidine methanesulphonate

Piperazine (149.2 g, 8 mol equiv) was heated to a melt and 1-(t-butoxycarbonyl)-3-methanesulphonyloxyazetidine (see (International Patent Application Publication No. WO93/19059) (54.5 g, 217 mmol)was then added. The mixture was heated at 115° C. for 24 hours, then cooled and the excess piperazine removed in vacuo. The residue was purified by flash chromatography (silica, methanol:dichloromethane, 1:19) to give the title compound (51 g).

LRMS m/z=242 (m+1)⁺.

¹H NMR (CDCl₃): 1.4 (m,9H); 2.5–2.6 (m,4H); 3.1–3.25 (m,5H); 3.7–3.8 (m,2H); 3.9–3.95 (m,2H); 4.6 (br, s, 1H) ppm.

2(b) 3-(4-Aminosulphonylpiperazin-1-yl)-1-(t-butoxycarbonyl)azetidine

A solution of the compound of Preparation 2(a) (50 g, 132.6 mmol) and sulphamide (88 g, 6.9 mol equiv) in 1,4-dioxane (1300 ml) was heated under reflux for 55 hours. The solution was cooled and the solvent removed in vacuo. The residue was purified by flash chromatography (silica, methanol:dichloromethane, 1:19) to give the title compound (50 g).

¹H NMR (CDCl₃): 1.45 (s,9H); 2.4–2.5 (m,4H); 3.1–3.2 (m,1 H); 3.25–3.3 (m,4H); 3.75–3.8 (m,2H); 3.85–3.9 (m,2H); 4.3 (br, s, 2H) ppm.

2(c) 3-(4-Aminosulphonylpiperazin-1-yl)azetidine bistrifluoroacetate

To a solution of the compound of Preparation 2(b) (364 mg, 1.14 mmol)in dichloromethane (6 ml) under nitrogen at 0° C. was slowly added trifluoroacetic acid (3 ml, 35 mol equiv) and the reaction mixture was allowed to warm to room temperature over 2 hours. The solvent was then removed in vacuo and the residue azeotroped with dichloromethane (3×10 ml). The resulting oil was triturated with diethyl ether to give the title compound (379 mg) which was used without further purification.

¹H NMR (CDCl₃): 2.4–2.6 (m,4H); 2.95–3.15 (m,4H); 3.35–3.5 (m,1H); 3.8–4.1 (m,4H), 6.6–6.8 (m,2H); 8.6–8.85 (m,3H) ppm.

PREPARATION 3,3-(4-Morpholinosulphonylpiperazin-1-yl)azetidine bistrifluoroacetate 3(a) Morpholinosulphamoyl chloride To a solution of sulphuryl chloride (27.7 ml, 3mol equiv) in acetonitrile (25 ml) under nitrogen was added a solution of morpholine (10 g, 114 mmol) in acetonitrile (25 ml). The reaction was heated under reflux for 15 hours, then cooled to room temperature and concentrated in vacuo to give the title compound (20.45 g).

LRMS m/z=211 (m+1)⁺.

¹H NMR (CDCl₃): 3.3–3.35 (m,4H); 3.8–3.85 (m,4H) ppm.

3(b) 1-(t-Butoxycarbonyl)-3-(4-morpholinosulphonylpiperazin-1-yl)azetidine

To a solution of the compound of Preparation 2(a) (2.2 g, 0.0103 mol) in acetonitrile (5 ml) under nitrogen was added triethylamine (2.15 ml, 1.5 mol equiv). A solution of the compound of Preparation 3(a) (210 mg, 1.1 mol equiv) in acetonitrile (10 ml) was added dropwise, and the reaction heated at reflux for 2 hours. The reaction was cooled to room temperature and the solvent removed in vacuo, the residue was partitioned between ethyl acetate (30 ml) and water (30 ml), the organic layer was washed with brine, dried over MgSO₄ and the solvent removed in vacuo. The residue was chromatographed (silica, methanol:dichloromethane, 1:9) to give the title compound.

LRMS m/z=391 (m+1)⁺.

¹H NMR (CDCl₃): 1.45 (s,9H); 2.4–2.45 (m,4H); 3.1–3.15 (m,1H); 3.2–3.35 (m,8H); 3.7–3.95 (m,8H) ppm.

3(c) 3-(4-Morpholinosulphonylpiperazin-1-yl)azetidine bistrifluoroacetate

To a solution of the compound of Preparation 3(b) (2.5 g, 6.878 mmol) in dichloromethane (35 ml) at 0° C. under nitrogen was added trifluoroacetic acid (7.95 ml), dropwise, the mixture was allowed to warm to room temperature and stirred for 1 hour. The mixture was reduced in vacuo, and the resulting gum washed with diethyl ether, then triturated with ethyl acetate and filtered to give the title compound as a yellow solid (2.63 g).

LRMS m/z=291 (m+1)⁺.

¹H NMR (d₆-DMSO): 2.4–2.5(m,4H), 3.1–3.25(m,7H), 3.35–3.4(m,1H), 3.6–3.65(m,3H), 3.8–4.05(m,4H), 8.7(s, br.,1H) ppm.

31

PREPARATION 4,3-(4-Piperidinosulphonylpiperazin-1-yl) azetidine

4(a) Piperidinosulphamoyl chloride

This was made by the same method as described above in Preparation 3(a) using piperidine and sulphuryl chloride.

4(b) 1-(t-Butoxycarbonyl)-3-(piperidinosulpbonylpiperazin-1-yl)azetidine

This was made by the same method as described above in Preparation 3(b) using the compounds of Preparations 2(a) and 4(a). The product was chromatographed (silica, methanol:dichloromethane, 1:9) to give the title compound as an oil, which was triturated with diethyl ether to give a yellow solid.

LRMS m/z=389.4 (m)$^+$.

$^1$H NMR (CDCl$_3$): 1.45 (s,9H); 1.5–1.6 (m,5H); 2.3–2.35 (m,4H); 3.0–3.2 (m,10H);.3.55–3.65 (m, 2H); 3.75–3.95 (m,2H) ppm.

4(c) 3-(4-(Piperidinosulphonyl)piperazin-1yl)azetidine bis-trifluoroacetate

This was made by the same method as described above in Preparation 3(c) using the compound of Preparation 4(b).

LRMS m/z=289 (m+1)$^+$.

$^1$H NMR (CDCl$_3$): 1.4–1.6 (m, 5H); 2.35–2.6 (m,5H); 3.05–3.2 (m, 8H); 3.3–3.45 (m,1H); 3.8–4.05(m,4H); 8.8 (br, s, 2H) ppm.

PREPARATION 5,2-Methanesulphonyloxyethylcyclopropane

To a solution of 2-cyclopropylethanol (2.1 g, 24.4 mmol) in dichloromethane (50 ml) at 0° C. under nitrogen was added triethylamine (4.1 ml, 1.3 mol equiv). Methanesulphonyl chloride (2.5 ml, 1.3 mol equiv) was added dropwise and the reaction stirred for 16 hours at room temperature. Water (30 ml) and dichloromethane (30 ml) were added. The organic phase was washed with water (2×50 ml) and then dried over anhydrous MgSO$_4$. The solution was then filtered and the solvent removed in vacuo to give the title compound as an oil (4.0 g).

LRMS m/z=1.82 (m+NH$_4$)$^+$.

$^1$H-NMR (CDCl$_3$): δ=0.1–0.15(m,2H), 0.5–0.55(m,2H), 0.7–0.8(m,1H), 1.6–1.7(m,2H), 3.00(s,3H), 4.25–4.3(m,2H) ppm.

PREPARATION 6,3-(4-Dimethylaminosulphonylpiperazin-1-yl)azetidine bistrifluoroacetate 6(a) Dimethylaminosulphamoyl chloride This was made by a similar method as described above in Preparation 3(a), using dimethylamine in place of morpholine.

$^1$H NMR (CDCl$_3$): 2.9 (s,6H) ppm.

6(b) 1-t-Butoxycarbonyl-3-(4-dimethylaminosulphonylpiperazin-1-yl)azetidine

This was prepared in a similar manner to that described in Preparation 3(b), using the compound of Preparation 6(a).

LRMS m/z=349 (m+1)$^+$.

$^1$H NMR (CDCl$_3$): 1.45 (s,9H); 2.4 (m,4H); 2.85 (m,6H); 3.1–3.2 (m,1H); 3.3–3.35 (m,4H); 3.75–3.95 (m,4H) ppm.

6(c) 3-(4-Dimethylaminosulphonylpiperazin-1-yl)azetidine bistrifluoroacetate

This was prepared in a similar manner to that described in Preparation 3(c), using the compound of Preparation 6(b).

LRMS m/z=249 (m+1)$^+$.

$^1$H NMR (d$_6$-DMSO): 2.4–2.5 (m,10H); 3.15–3.2 (m,4H); 3.35–3.45 (m,1H); 3.8–4.05 (m,4H); 8.75 (br, s, 1H) ppm.

PHARMACOLOGICAL DATA

The compound of Example 3 was tested for NK$_2$ receptor binding activity by the in vitro method described earlier, and it had a pIC$_{50}$ of 9.3. This compound was also tested for NK$_2$ receptor antagonist activity by the in vitro method of Patacchini and Maggi mentioned earlier, and it had a pA$_2$ of 8.1

We claim:

1. A compound of the formula (I):

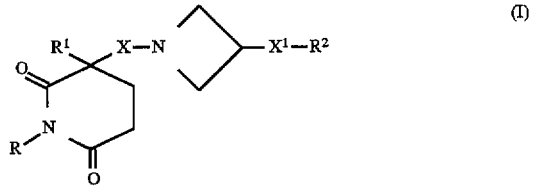

or a pharmaceutically acceptable salt thereof, wherein

R is C$_3$–C$_7$ cycloalkyl, aryl or C$_1$–C$_6$ alkyl, said C$_1$–C$_6$ alkyl being optionally substituted by fluoro, —COOH, —COO(C$_1$–C$_4$) alkyl, C$_3$–C$_7$ cycloalkyl, adamantyl, aryl or het$^1$, and said C$_3$–C$_7$ cycloalkyl being optionally substituted by 1 or 2 substituents each independently selected from C$_1$–C$_4$ alkyl, C$_3$–C$_7$ cycloalkyl, C$_1$–C$_4$ alkoxy, hydroxy, fluoro, fluoro(C$_1$–C$_4$) alkyl and fluoro (C$_1$–C$_4$)alkoxy;

R$^1$ is phenyl, benzyl, naphthyl, thienyl, benzothienyl or indolyl, each optionally substituted by 1 or 2 substituents each independently selected from C$_1$–C$_4$ alkyl, C$_1$–C$_4$ alkoxy, halo and trifluoromethyl;

R$^2$ is —CO$_2$H, —CONR$^3$R$^4$, —CONR$^5$(C$_3$–C$_7$ cycloalkyl), —NR$^5$(C$_2$–C$_5$ alkanoyl), —NR$^3$R$^4$, —NR$^5$CONR$^5$R$^6$, (C$_3$–C$_7$ cycloalkyl-C$_1$–C$_4$ alkyl) R$^5$N—, (C$_3$–C$_7$ cycloalkyl-C$_1$–C$_4$ alkyl)$_2$N, —NR$^5$COCF$_3$, —NR$^5$SO$_2$CF$_3$, —NR$^5$(SO$_2$C$_1$–C$_4$ alkyl), —NR$^5$SO$_2$NR$^5$R$^6$, —NR$^5$(SO$_2$ aryl), —N(aryl) (SO$_2$C$_1$–C$_4$ alkyl), —OR$^5$, —O(C$_3$–C$_7$ cycloalkyl), —SO$_2$NR$^5$R$^6$, het$^3$ or a group of the formula:

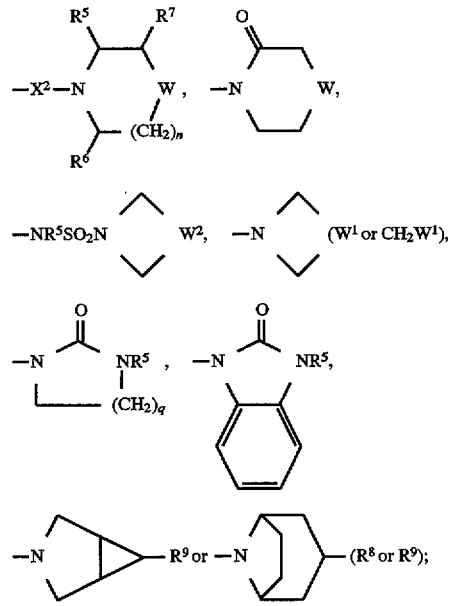

R$^3$ and R$^4$ are each independently selected from H and C$_1$–C$_4$ alkyl optionally substituted by hydroxy, C$_1$–C$_4$ alkoxy, —S(O)$_p$(C$_1$–C$_4$ alkyl), amino, —NH(C$_1$–C$_4$ alkyl), —N(C$_1$–C$_4$ alkyl)$_2$ or het$^2$;

R$^5$ and R$^6$ are each independently selected from H, C$_1$–C$_4$ alkyl and C$_3$–C$_7$ cycloalkyl-C$_1$–C$_4$ alkyl, said C$_1$–C$_4$ alkyl and C$_3$–C$_7$ cycloalkyl-C$_1$–C$_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5(SO_2C_1$–$C_4$ alkyl), —$NR^5SO_2NR^5R^6$, —$NR^5COO(C_1$–$C_4$ alkyl), —$NR^5CONR^5R^6$, —$NR^5(SO_2$morpholino), —$NR^5(SO_2$ aryl), —N(aryl)($SO_2C_1$–$C_4$ alkyl) or a group of the formula:

—NR⁵SO₂N⟨△⟩(CH₂)ᵣ;

X is $C_1$–$C_4$ alkylene;

$X^1$ is a direct link or $C_1$–$C_6$ alkylene;

$X^2$ is a direct link, CO, $SO_2$ or $NR^5CO$ where the carbonyl is attached to the ring nitrogen atom;

W is methylene, CO, CH(OH), C(OH)$_2$, CH($C_1$–$C_4$ alkoxy), CHCO$_2$H, CHCO$_2$($C_1$–$C_4$ alkyl), CHCONR$^5$R$^6$, CHF, CF$_2$, CH(azetidin-1-yl), CH(pyrrolidin-1-yl), CH(piperidin-1-yl), CH(morpholino), CH(benzoxazol-2-yl), CHR$^9$, O, S(O)$_p$, NR$^5$, N(C$_3$–C$_7$ cycloalkyl), NSO$_2$(C$_1$–C$_4$ alkyl), NSO$_2$NR$^5$R$^6$, NSO$_2$CF$_3$, NSO$_2$(morpholino), NSO$_2$(aryl),

—NSO₂N⟨△⟩(CH₂)ᵣ,

NCONR$^5$R$^6$, NCOR$^5$, NCO(aryl) or NCO$_2$(C$_1$–C$_4$ alkyl);

$W^1$ is methylene, CO, CH(OH), C(OH)$_2$, CH($C_1$–$C_4$ alkoxy), CHCO$_2$H, CHCO$_2$($C_1$–$C_4$ alkyl), CHCONR$^5$R$^6$, CHF, CF$_2$, CH(azetidin-1-yl), CH(pyrrolidin-1-yl), CH(piperidin-1-yl), CH(morpholino) or CHR$^9$;

$W^2$ is $W^1$, —CH$_2$W$^1$—, —CH$_2$WCH$_2$— or —CH$_2$CH$_2$WCH$_2$—;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R^9$ and W, means naphthyl or phenyl, each optionally substituted by $C_1$–$C_4$ alkyl, halo, —$OR^5$, fluoro($C_1$–$C_4$)alkyl, $C_2$–$C_5$ alkanoyl, —$CONR^5R^6$, —$SO_2NR^5R^6$ or phenyl;

"het$^1$", used in the definition of R, means thienyl or a 5- or 6-membered ring heteroaryl group containing either 1 or 2 nitrogen heteroatoms or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro($C_1$–$C_4$ alkyl) and fluoro($C_1$–$C_4$ alkoxy);

"het$^2$", used in the definitions of $R^3$ and $R^4$, means a 4- to 7-membered ring, non-aromatic, heterocyclic group containing 1 or 2 heteroatoms each independently selected from nitrogen, oxygen and S(O)$_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —$CONR^5R^6$ or —$SO_2NR^5R^6$ substituent;

and "het$^3$", used in the definition of $R^2$, means an optionally benzo-fused, N-linked, 5-membered ring heteroaryl group containing from 1 to 4 nitrogen heteroatoms, which het$^3$ is optionally substituted, including in the benzo-fused portion, by 1 or 2 substituents each independently selected from $C_1$–$C_4$ alkyl, fluoro and fluoro($C_1$–$C_4$)alkyl.

2. A compound or salt according to claim 1 wherein R is aryl, optionally substituted $C_3$–$C_7$ cycloalkyl, or is $C_1$–$C_6$ alkyl substituted by aryl or optionally substituted $C_3$–$C_7$ cycloalkyl.

3. A compound or salt according to claim 1 wherein $R^1$ is phenyl optionally substituted by 1 or 2 halo substituents.

4. A compound or salt according to claim 1 wherein $R^2$ is —$CONR^3R^4$, —$CONR^5$($C_3$–$C_7$ cycloalkyl), —$NR^3R^4$, het$^3$ or a group of the formula:

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CHF, CO, CH($C_1$–$C_4$ alkoxy), CHCO$_2$H, CHCO$_2$($C_1$–$C_4$ alkyl), CH(benzoxazol-2-yl), CHNR$^5$R$^6$, CHNR$^5$COR$^5$, CHNR$^5$(SO$_2$C$_1$–C$_4$ alkyl), CHNR$^5$COO($C_1$–$C_4$ alkyl), O, S(O)$_p$, NR$^5$, NSO$_2$($C_1$–$C_4$ alkyl), NSO$_2$NR$^5$R$^6$, NSO$_2$(morpholino), NSO$_2$(piperidino), NCONR$^5$R$^6$, NCOR$^5$, NCO(aryl) or NCO$_2$($C_1$–$C_4$ alkyl), n is 1 or 2 when W is other than methylene and is 0 or 1 when W is methylene, and p is 0, 1 or 2.

5. A compound or salt according to claim 1 wherein X is ethylene or propylene.

6. A compound or salt according to claim 1 wherein $X^1$ is a direct link.

7. A compound or salt according to claim 1 wherein R is optionally substituted $C_3$–$C_7$ cycloalkyl or $C_1$–$C_6$ alkyl substituted by optionally substituted $C_3$–$C_7$ cycloalkyl.

8. A compound or salt according to claim 1 wherein $R^1$ is phenyl optionally substituted by 1 or 2 substituents each independently selected from fluoro and chloro.

9. A compound or salt according to claim 1 wherein $R^2$ is —$CONR^3R^4$, —$CONR^5$($C_3$–$C_7$ cycloalkyl), —$NR^3R^4$, a N-linked, 5-membered ring heteroaryl group containing 1 or 2 nitrogen heteroatoms, or a group of the formula:

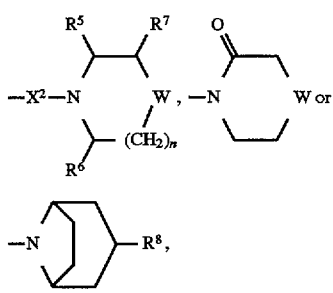

where $R^3$ and $R^4$ are each independently selected from methyl and $C_1$–$C_4$ alkyl substituted by hydroxy or methoxy, $R^5$ and $R^6$ are each independently selected from H, methyl, trifluoromethyl and cyclopropylmethyl, $R^7$ is H, hydroxy or phenyl, $R^8$ is hydroxy or acetyloxy, W is methylene, CH(OH), CHOCH$_3$, CHF, CO, CHOCH$_2$CH$_3$, CHO(CH$_2$)$_2$CH$_3$, CHOC(CH$_3$)$_3$, CHCO$_2$H, CHCO$_2$CH$_3$, CHCO$_2$CH$_2$CH$_3$, CH(benzoxazol-2-yl), CHNH$_2$, CHNHCH$_2$(cyclopropyl), CHNHCOCH$_3$, CHNHSO$_2$CH$_3$, CHNHCO$_2$C(CH$_3$)$_3$, O, S(O)$_p$, NH, NCH$_3$, NCH$_2$(cyclopropyl), NSO$_2$CH$_3$, NSO$_2$NH$_2$, NSO$_2$NHCH$_3$, NSO$_2$N(CH$_3$)$_2$, NSO$_2$(morpholino), NSO$_2$(piperidino), NCONH$_2$, NCONHCH$_3$, NCOCH$_3$, NCOCF$_3$, NCO (phenyl) or NCO$_2$C(CH$_3$)$_3$, n is 1 or 2 when W is other than methylene and is 0 or 1 when W is methylene, and p is 0, 1 or 2.

10. A compound or salt according to claim 9 wherein $R^2$ is a group of the formula:

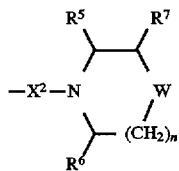

where $R^5$, $R^6$, $R^7$, W and n are as defined in claim 9, and $X^2$ is a direct link.

11. A compound or salt according to claim 1 wherein R is 2-cyclopropylethyl, cyclohexyl, 4,4-difluorocyclohexyl, cyclohexylmethyl or cyclopropylmethyl.

12. A compound or salt according to claim 1 wherein $R^1$ is phenyl, 3,4-difluorophenyl, 3-chlorophenyl, 4-chlorophenyl or 3,4-dichlorophenyl.

13. A compound or salt according to claim 1 or claim 11 or 12, wherein $R^2$ is N-(2-methoxyethyl)-N-methylcarbamoyl, N-cyclohexylcarbamoyl, N-(2-hydroxyethyl)-N-methylamino, N-(2-hydroxy-2-methylpropyl)-N-methlamino, N-(2-methoxyethyl)-N-methylamino, imidazol-1-yl, 3-hydroxypyrrolidin-1-yl, piperidin-1-yl, 2,6-dimethylpiperidin-1-yl, 3-hydroxypiperidin-1-yl, 4-hydroxypiperidin-1-yl, 4-methoxypiperidin-1-yl, 4-ethoxypiperidin-1-yl, 4-(n-propoxy)piperidin-1-yl, 4-(t-butoxy)piperidin-1-yl, 4-carboxypiperidin-1-yl, 4-methoxycarbonylpiperidin-1-yl, 4-ethoxycarbonylpiperidin-1-yl, 4-(benzoxazol-2-yl) piperidin-1-yl, 4-aminopiperidin-1-yl, 4-cyclopropylmethylaminopiperidin-1-yl, 4-acetamidopiperidin-1-yl, 4-methanesulphonamidopiperidin-1-yl, 4-(t-butoxycarbonylamino)piperidin-1-yl, morpholino, 2-phenylmorpholino, homomorpholino, thiomorpholino, 1-oxothiomorpholino,1,1-dioxothiomorpholino, piperazin-1-yl, 4-methylpiperazin-1-yl, 4-cyclopropylmethylpiperazin-1-yl, 4-methanesulphonylpiperazin-1-yl, 4-aminosulphonylpiperazin-1-yl, 4-methylaminosulphonylpiperazin-1-yl, 4-dimethylaminosulphonylpiperazin-1-yl, 4-morpholinosulphonylpiperazin-1-yl, 4-piperidinosulphonylpiperazin-1-yl, 4-carbamoylpiperazin-1-yl, 4-N-methylacarbamoylpiperazin-1-yl, 4-acetylpiperazin-1-yl, 4-trifluoroacetylpiperazin-1-yl, 4-benzoylpiperazin-1-yl, 4-(t-butyoxycarbonyl)piperazin-1-yl, pyrrolidin-1-ylcarbonyl, piperidin-1-ylcarbonyl, 3-oxomorpholino, 3-hydroxy-8-azabicyclo[3.2.1]oct-8-yl, 3-acetyloxy-8-azabicyclo[3.2.1]oct-8-yl, 4-fluoropiperidin-1-yl or 4-oxopiperidin-1-yl.

14. A compound or salt according to claim 1 wherein $R^1$ is 3,4-dichlorophenyl.

15. A compound or salt according to claim 1 wherein $R^2$ is 4-aminopiperidin-1-yl, 4-carboxypiperidin-1-yl, 4-hydroxypiperidin-1-yl, morpholino, 1-oxothiomorpholino, 4-aminosulphonylpiperazin-1-yl, 4-methanesulphonylpiperazin-1-yl, 4-dimethylaminosulphonylpiperazin-1-yl, 4-morpholinosulphonylpiperazin-1-yl, 4-piperidinosulphonylpiperazin-1-yl, 4-fluoropiperidin-1-yl or 4-oxopiperidin-1-yl.

16. A compound or salt according to claim 1 wherein (i) R is cyclohexylmethyl, $R^1$ is 3,4-dichlorophenyl, X is ethylene, $X^1$ is a direct link and $R^2$ is morpholino;

(ii) R is cyclohexylmethyl, $R^1$ is 3,4-dichlorophenyl, X is ethylene, $X^1$ is a direct link and $R^2$ is 4-aminosulphonylpiperazin-1-yl;

(iii) R is cyclopropylmethyl, $R^1$ is 3,4-dichlorophenyl, X is ethylene, $X^1$ is a direct link and $R^2$ is 4-morpholinosulphonylpiperazin-1-yl;

(iv) R is cyclopropylmethyl, $R^1$ is 3,4-dichlorophenyl, X is ethylene, $X^1$ is a direct link and $R^2$ is 4-aminosulphonylpiperazin-1-yl;

(v) R is cyclopropylmethyl, $R^1$ is 3,4-dichlorophenyl, X is ethylene, $X^1$ is a direct link and $R^2$ is 4-dimethylaminosulphonylpiperazin-1-yl;

(vi) R is cyclopropylmethyl, $R^1$ is 3,4-dichlorophenyl, X is ethylene, $X^1$ is a direct link and $R^2$ is 4-piperidinosulphonylpiperazin-1-yl;

(vii) R is cyclopropylethyl, $R^1$ is 3,4-dichlorophenyl, X is ethylene, $X^1$ is a direct link and $R^2$ is 4-aminosulphonylpiperazin-1-yl; or (viii) R is cyclopropylethyl, $R^1$ is 3,4-dichlorophenyl, X is ethylene, $X^1$ is a direct link and $R^2$ is morpholino.

17. A compound or salt according to claim 1 wherein the compound of formula (I) has the stereochemistry shown below in formula (IA) at the position of attachment of the X and $R^1$ groups to the glutarimide ring:

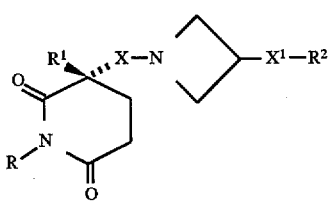
(IA)

18. A pharmaceutical composition comprising a compound or salt according to claim 1 and a pharmaceutically acceptable diluent or carrier.

19. A method of treatment of a human to treat a disease by producing an antagonist effect on a tachykinin acting at the human neurokinin-1 ($NK_1$), human neurokinin-2 ($NK_2$) or human neurokinin-3 ($NK_3$) receptor, or a combination of two or more thereof, which comprises treating said human with an effective amount of a compound or salt according to claim 1.

20. A method according to claim 19 wherein the disease is an inflammatory disease, a central nervous system disorder, a gastro-intestinal disorder, a urogenital tract disorder, a pulmonary disorder, an allergy disorder, a hypersensitivity disorder, a peripheral neuorpathy disorder, cough or acute or chronic pain.

* * * * *